United States Patent
Morales et al.

(10) Patent No.: US 10,973,816 B2
(45) Date of Patent: *Apr. 13, 2021

(54) CRYSTALLIZATION PROCESS OF ARIPIPRAZOLE DERIVATIVES IN EXTENDED RELEASE FORMULATIONS FOR TREATMENT OF SCHIZOPHRENIA

(71) Applicant: ALKERMES PHARMA IRELAND LIMITED, Dublin (IE)

(72) Inventors: Wilfredo Morales, Morrow, OH (US); Tarek A. Zeidan, Lexington, MA (US); Renato A. Chiarella, Cambridge, MA (US); Steven G. Wright, Madeira, OH (US); Jason M. Perry, Cambridge, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,608

(22) Filed: Oct. 8, 2019

(65) Prior Publication Data

US 2020/0108063 A1 Apr. 9, 2020

Related U.S. Application Data

(63) Continuation of application No. 16/043,721, filed on Jul. 24, 2018, now Pat. No. 10,478,434, which is a continuation of application No. 14/833,638, filed on Aug. 24, 2015, now Pat. No. 10,064,859.

(60) Provisional application No. 62/041,341, filed on Aug. 25, 2014.

(51) Int. Cl.
  *A61K 31/496* (2006.01)
  *A61K 31/00* (2006.01)
  *C07D 401/12* (2006.01)

(52) U.S. Cl.
  CPC ............ *A61K 31/496* (2013.01); *A61K 31/00* (2013.01); *C07D 401/12* (2013.01)

(58) Field of Classification Search
  CPC ..... A61K 31/496; A61K 31/00; C07D 401/12
  USPC ....................................................... 544/362
  See application file for complete search history.

(56) References Cited

U.S. PATENT DOCUMENTS

| | | | |
|---|---|---|---|
| 5,510,118 A | 4/1996 | Bosch et al. | |
| 8,431,576 B2 | 4/2013 | Remenar et al. | |
| 9,034,867 B2 | 8/2015 | Perry et al. | |
| 10,064,859 B2 * | 9/2018 | Morales, Jr. ......... | A61K 31/496 |
| 10,478,434 B2 * | 11/2019 | Morales ............... | A61K 31/496 |
| 2005/0032811 A1 | 2/2005 | Brown | |
| 2009/0163519 A1 | 6/2009 | Vermeulen et al. | |
| 2011/0003823 A1 | 1/2011 | Blumberg et al. | |
| 2012/0238552 A1 | 9/2012 | Perry et al. | |
| 2012/0316180 A1 | 12/2012 | Bando et al. | |
| 2013/0096089 A1 | 4/2013 | Remenar et al. | |

OTHER PUBLICATIONS

Akers, M. et al., (1987) "Formulation Design and Development of Parenteral Suspensions," journal of Parenteral Science. 41(3):88-96.
FDA approves new injectable drug to treat schizophrenia, (Oct. 6, 2015) FDA news release.
Gowda et al. (2013) "Development and characterization of ground mixtures of aripiprazole with hydrophilic carriers," International journal of Pharmaceutical Research and Bio-Science. 2(6):537-556.
International Search Report with Written opinion corresponding to International Patent Application No. PCT/US2015/046525, dated Nov. 30, 2015.
Kesisoglou et al. (2007) "Nanosizing: oral formulation development and biopharmaceutical evaluation," Advanced Drug Delivery Reviews. 59(7):631-633.
Leonard et al. (1995) Advanced Practical Organic Chemistry, 2nd ed., Chapter 9, pp. 128-226.
Marszall, L. et al. (1982) "The effect of glycols on the hydrophile-lipophile balance and the micelle formation of nonionic surfactants," JAOCS. 59(2):84-87.
Morales et al. (2012) "Mechanical Particle-Size Reduction Techniques," AAPS Advances in Pharmaceutical Sciences Series: Formulating Poorly Water Soluble Drugs. pp. 133-170.
Pharmaceutical Dosage Forms: Disperse Systems, vol. 2, $2^{nd}$ edition. (1996) Edited by Lieberman et al., pp. 18-22 & 285-301.
Pharmaceutics: The Science of Dosage Form Design, Drug Delivery Systems. (1988) Edited by Aulton. Chapter 23: Suspensions and Emulsions, pp. 334-359.
Pharmaceutics: The Science of Dosage Form Design, Drug Delivery Systems. (1988) Edited by Aulton. pp. 272-274 and 278.
Shintani, S. et al. (1967) "A New Method to Determine the Irritation of Drugs After Intramuscular Injection in Rabbits," Toxicology and Applied Pharmacology. 11:293-301.
The HLB System: a time-saving guide to emulsifier selection, (1984) Chapter 5. ICI Americas Inc. Wilmington, DE.
U.S. Appl. No. 13/423,606 / 2012/0238552 / U.S. Pat. No. 9,034,867, filed Mar. 19, 2012 / Sep. 20, 2012 / May 19, 2015, Jason M. Perry.
U.S. Appl. No. 14/714,621 / 2015/0258115 / U.S. Pat. No. 9,351,976, filed May 18, 2015 / Sep. 17, 2015 / May 31, 2016, Jason M. Perry.
U.S. Appl. No. 15/388,554 / 2017/0196856 / U.S. Pat. No. 10,226,458, filed Dec. 22, 2016 / Jul. 13, 2017 / Mar. 12, 2019, Jason M. Perry.
U.S. Appl. No. 16/248,259 / 2019/0216805, filed Jan. 15, 2019 / Jul. 18, 2019, Jason M. Perry.
U.S. Appl. No. 13/801,025 / 2013/0267503 / U.S. Pat. No. 10,004,807, filed Mar. 13, 2013 / Oct. 10, 2013 / Jun. 26, 2018, Jason M. Perry.
U.S. Appl. No. 13/801,167 / 2013/0267504 / U.S. Pat. No. 9,993,556, filed Mar. 13, 2013 / Oct. 10, 2013 / Jun. 12, 2018, Jason M. Perry.

(Continued)

*Primary Examiner* — Tracy Vivlemore
*Assistant Examiner* — Ebenezer O Sackey
(74) *Attorney, Agent, or Firm* — Lathrop GPM LLP; Brian C. Trinque

(57) ABSTRACT

Processes for providing depot injections of recrystallized aripiprazole lauroxil in which particles of the aripiprazole lauroxil have a surface area of about 0.50 to about 3.3 m²/g; and crystals of aripiprazole lauroxil produced by such processes.

24 Claims, 19 Drawing Sheets

(56) References Cited

OTHER PUBLICATIONS

U.S. Appl. No. 13/801,344 / 2013/0267505 / U.S. Pat. No. 9,999,670, filed Mar. 13, 2013 / Oct. 10, 2013 / Jun. 19, 2018, Jason M. Perry.
U.S. Appl. No. 14/031,842 / 2014/0088115 / U.S. Pat. No. 9,193,685, filed Sep. 19, 2013 / Mar. 27, 2014 / Nov. 24, 2015, Jason M. Perry.
U.S. Appl. No. 14/882,069 / 2016/0136279 / U.S. Pat. No. 9,861,699, filed Oct. 13, 2015 / May 19, 2016 / U.S. Pat. No. 9,861,699, Jason M. Perry.
U.S. Appl. No. 15/705,237 / 2018/0000944 / U.S. Pat. No. 10,342,877, filed Sep. 14, 2017 / Jan. 4, 2018 / Jul. 9, 2019, Jason M. Perry.
U.S. Appl. No. 16/425,150 / 2019/0275155, filed May 29, 2019 / Sep. 12, 2019, Jason M. Perry.
U.S. Appl. No. 14/663,042 / 2015/0265529 / U.S. Pat. No. 9,452,131, filed Mar. 19, 2015 / Sep. 24, 2015 / Sep. 27, 2016, Magali B. Hickey.
U.S. Appl. No. 15/164,473 / 2016/0263111 / U.S. Pat. No. 9,526,726, filed May 25, 2016 / Sep. 15, 2016 / Dec. 27, 2016, Magali B. Hickey.
U.S. Appl. No. 15/349,243 / 2017/0157117 / U.S. Pat. No. 10,085,980, filed Nov. 11, 2016 / Jun. 8, 2017 / Oct. 2, 2018, Magali B. Hickey.
U.S. Appl. No. 16/116,652 / 2018/0369239 / U.S. Pat. No. 10,238,651, filed Aug. 29, 2018 / Dec. 27, 2018 / Mar. 26, 2019, Magali B. Hickey.
U.S. Appl. No. 16/271,248 / 2019/0167673, filed Feb. 8, 2019 / Jun. 6, 2019, Magali B. Hickey.
U.S. Appl. No. 14/833,638 / 2016/0051546 / U.S. Pat. No. 10,064,859, filed Aug. 24, 2015 / Feb. 25, 2016 / Sep. 4, 2018, Wilfredo Morales.
U.S. Appl. No. 16/043,721 / 2019/0015408 / U.S. Pat. No. 10,478,434, filed Jul. 24, 2018 / Jan. 17, 2019 / Nov. 19, 2019, Wilfredo Morales.
Aulton's Pharmaceutics, The Design and manufacture of medicines, Third edition. Course Disperse Systems, 2007, pp. 90-90 & 386-388.
Handbook of Pharmaceutical Excipients, Fifth edition. Edited by Rowe et al. Extract for Sorbitan Esters.2006, pp. 473-476.
Handbook of Pharmaceutical Excipients, Sixth edition. Edited by Rowe et al. Extract for Sorbitan Esters. 2009, pp. 675-678.
The Pharmaceutical Codex. Twelfth Edition, Edited by W. Lund, Suspensions, 1994, pp. 72-87.

* cited by examiner

CRYSTALLIZATION PROCESS OF ARIPIPRAZOLE DERIVATIVES IN EXTENDED RELEASE FORMULATIONS FOR TREATMENT OF SCHIZOPHRENIA

RELATED APPLICATIONS

This application claims priority to U.S. Provisional Application Ser. No. 62/041,341, filed on Aug. 25, 2014, the content of which is incorporated herein by reference in its entirety.

FIELD OF THE INVENTION

The present invention is directed to the preparation of crystalline forms of aripiprazole derivatives including aripiprazole lauroxil and aripiprazole cavoxil. More particularly, the present invention is directed to controlling the recrystallization of aripiprazole lauroxil and aripiprazole cavoxil to produce particles useful in extended release injectable formulations for the treatment of schizophrenia and other psychiatric conditions.

RELATED ART

Aripiprazole is an atypical antipsychotic drug used in the treatment of schizophrenia and other psychiatric conditions, such as bipolar disorder and major depressive disorder. Aripiprazole, which is a dopamine $D_2$ and serotonin $5\text{-}HT_{1A}$ receptor agonist, and an antagonist of the serotonin $5\text{-}HT_{2A}$ receptor, has been formulated as a tablet and as a solution, both for oral administration. However, concerns with patient compliance with oral antipsychotics have been reported, and other methods of delivering antipsychotics, such as intramuscular or subcutaneous injection, have been developed. ABILIFY®, which is a drug containing aripiprazole as the active agent, is available from Otsuka as an oral tablet (aripiprazole dosage of 2 mg, 5 mg, 10 mg, 15 mg, 20 mg, or 30 mg), an orally disintegrating tablet (dosage of 10 mg or 15 mg), an oral solution (dosage of 1 mg/mL), and as an injection for intramuscular use (9.75 mg/1.3 mL in a single-dose vial). ABILIFY® is indicated for schizophrenia, bipolar I disorder, adjunctive treatment of major depressive disorder, irritability associated with autistic disorder, and agitation associated with schizophrenia or bipolar mania. Abilify Maintena® is an extended release injectable suspension of aripiprazole available from Otsuka, and which is indicated for schizophrenia.

There is a need in the art for formulations containing an aripiprazole prodrug that when administered to a patient can provide for improved therapeutic amounts of aripiprazole.

There is also a need in the art for methods of preparing an aripiprazole prodrug that can be formulated into a long-acting or extended-release formulation that when administered to a patient can provide for improved therapeutic amounts of aripiprazole over an extended period of time.

SUMMARY OF THE INVENTION

The present invention provides a process for making a compound of Formula (A) in crystal form

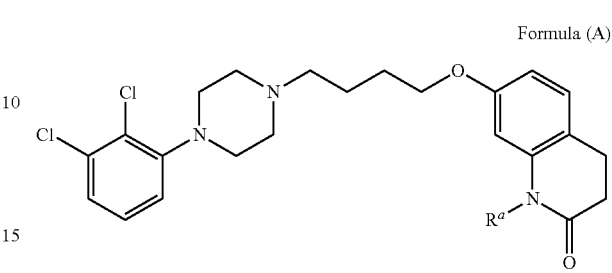

Formula (A)

wherein $R^a$ is $CH_2OC(O)R^1$ and wherein $R^1$ is a substituted or unsubstituted aliphatic moiety, comprising the steps of:

(a) obtaining a drug solution by combining the compound of Formula (A) or a salt or solvate thereof with a first solvent;

(b) optionally combining the drug solution with a second solvent to form a mixture;

(c) cooling the mixture; and (d) when the temperature of the mixture is within the range of about 0-5° C. above a target temperature, homogenizing the mixture to form crystallized particles of the compound of Formula (A) having a surface area of about 0.50 m²/g to about 3.3 m²/g.

In another embodiment of the method, the compound of Formula (A) is selected from the group consisting of:

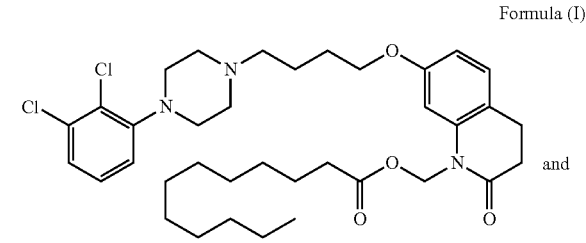

Formula (I)

and

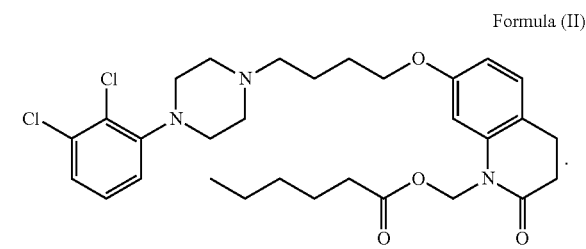

Formula (II)

In a particular embodiment of the method, the compound of Formula (A) has the structure of Formula (I). In another particular embodiment, the compound of Formula (A) has the structure of Formula (II).

The present invention provides a process for making a compound of Formula (I) in crystal form

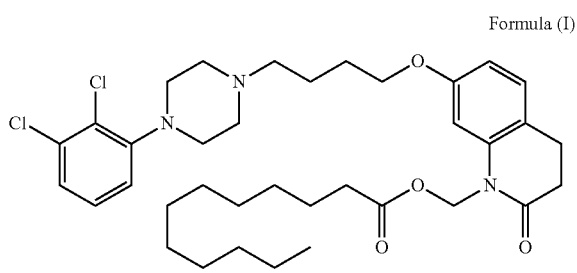 [SMILES: CCCCCCCCCCCC(=O)OCN1C(=O)CCc2ccc(OCCCCN3CCN(c4cccc(Cl)c4Cl)CC3)cc21]

Formula (I)

comprising the steps of:

(a) obtaining a drug solution by combining the compound of Formula (A) or a salt or solvate thereof with a first solvent;

(b) optionally combining the drug solution with a second solvent to form a mixture;

(c) cooling the mixture; and (d) when the temperature of the mixture is within the range of about 0-5° C. above a target temperature, homogenizing the mixture to form crystallized particles of the compound of Formula (A) having a surface area of about 0.50 $m^2/g$ to about 3.3 $m^2/g$.

The present invention also provides a process for making a compound of Formula (II) in crystal form

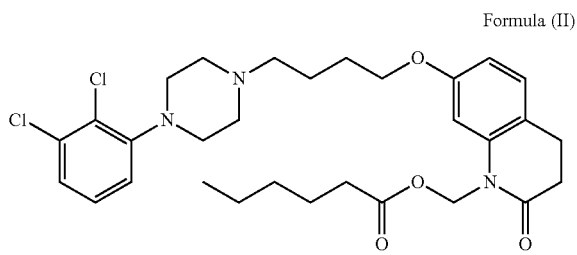 [SMILES: CCCCCC(=O)OCN1C(=O)CCc2ccc(OCCCCN3CCN(c4cccc(Cl)c4Cl)CC3)cc21]

Formula (II)

comprising the steps of:

(a) obtaining a drug solution by combining the compound of Formula (A) or a salt or solvate thereof with a first solvent;

(b) optionally combining the drug solution with a second solvent to form a mixture;

(c) cooling the mixture; and (d) when the temperature of the mixture is within the range of about 0-5° C. above a target temperature, homogenizing the mixture to form crystallized particles of the compound of Formula (A) having a surface area of about 0.50 $m^2/g$ to about 3.3 $m^2/g$.

The processes provided herein encompass a number of embodiments, including the following:

In one embodiment, the first solvent of step (a) is a single solvent. In another embodiment, the first solvent of step (a) is a mixture of two or more solvents. In a particular embodiment, the first solvent of step (a) is a mixture of two or more solvents and step (b) is absent. Suitable solvents are known to persons having skill in the art of crystallization. Examples of solvents are provided infra. In a particular embodiment, the first solvent of step (a) is isopropyl acetate. In another particular embodiment, the first solvent of step (a) is a mixture of isopropyl acetate and n-heptane.

In one embodiment, step (b) comprises combining the drug solution with a second solvent to form a mixture. In a particular embodiment, the second solvent of step (b) is n-heptane.

The mixture of step (b) may be a homogeneous mixture. In certain embodiments, homogeneity of the mixture of step (b) is achieved or maintained by heating or preheating the first solvent of step (a) and/or the drug solution of step (a) and/or the second solvent of step (b). In a particular embodiment, the temperature of the mixture of step (b) is in the range of about 55° C. to about 65° C. In another embodiment, step (b) is absent. When step (b) is absent, step (c) comprises cooling the drug solution of step (a), and step (d) comprises homogenizing the drug solution to form crystallized particles of the compound of Formula (A) having a surface area of about 0.50 $m^2/g$ to about 3.3 $m^2/g$ when the temperature of the mixture is within the range of about 0-5° C. above a target temperature, In one embodiment, step (c) comprises cooling the mixture to the point of supersaturation. The temperature at which the mixture becomes supersaturated may be in the range of about 50° C. to about 55° C. In another embodiment, step (c) comprises cooling to mixture to so that its temperature approaches a target temperature. In a particular embodiment, the target temperature is about 34° C.

In one embodiment, the target temperature of step (d) is in the range of about 31° C. to about 35° C. In a particular embodiment, the target temperature of step (d) is about 34° C. In another embodiment of step (d), homogenizing begins when the temperature of the mixture is about 0° C. to about 4° C. above the target temperature (e.g., at about 31° C. to about 38° C.).

The foregoing methods may further comprise the following steps:

(e) stopping homogenization and re-dissolving the crystallized particles of the compound of Formula (A) (e.g., compounds having the structure of Formula (I) or Formula (II)) by heating the mixture;

(f) cooling the mixture; and (g) when the temperature of the mixture is within the range of about 0-5° C. above the target temperature, homogenizing the mixture to form crystallized particles of the compound of Formula (A) (e.g., compounds having the structure of Formula (I) or Formula (II)) having a surface area of about 0.50 $m^2/g$ to about 3.3 $m^2/g$.

Steps (c), (d) and (e) may be performed once, or two or more times, prior to proceeding to step (f).

Any one or more of steps (a), (b), (c), (d), (e), and (f) may be performed under agitation The foregoing methods may further comprise the following steps: filtering the crystallized particles; rinsing the crystallized particles; and drying the crystallized particles.

The crystallized particles produced in accordance with the processes described herein may have a surface area of about 0.80 to about 1.1 $m^2/g$. In one embodiment, the crystallized particles have a surface area of about 1.00 $m^2/g$. In another embodiment, the Dv[50] of the crystallized particles is about 10 to about 30 microns. In still another embodiment, the Dv[50] of the crystallized particles is about 10 to about 20 microns. In yet another embodiment, the crystallized particles are suitable for use in a depot injection.

The invention provides crystallized particles of the compound of Formula (I) and the compound of Formula (II) produced by the foregoing process. Preferably, the crystallized particles may have a surface area of about 0.80 to about 1.1 $m^2/g$, and more preferably, about 1.00 $m^2/g$. The Dv[50] of the crystallized particles may be about 10 to about 30 microns, preferably about 10 to about 20 microns.

The present invention provides a process for providing a depot injection comprising the compound of Formula (I) in crystal form

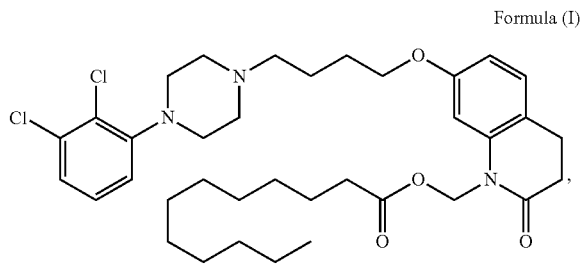 [SMILES: CCCCCCCCCCCC(=O)OCN1C(=O)CCc2ccc(OCCCCN3CCN(c4cccc(Cl)c4Cl)CC3)cc21]

Formula (I)

the process comprising the steps of: (a) obtaining a drug solution by combining the compound of Formula (I) or a salt or solvate thereof with a first solvent; (b) combining the drug solution with a second solvent to form a mixture with reduced solubility relative to the solubility of the drug solution; (c) cooling the mixture so that it becomes supersaturated; (d) cooling the mixture so that its temperature approaches a target temperature; and (e) when the temperature of the mixture is within the range of about 5° C. above the target temperature, homogenizing the mixture to form crystallized particles of the compound of Formula (I) having a surface area of about 0.50 to about 3.3 m$^2$/g. Any one or more of steps (a) through (d) of the foregoing process may be performed under agitation. The foregoing process may further comprise the steps of (f) filtering the crystallized particles, (g) rinsing the crystallized particles, and (h) drying the crystallized particles.

In the foregoing process, the first solvent may be ethyl acetate, propyl acetate, isopropyl acetate, butyl acetate, isobutyl acetate, tert-butyl acetate, acetone, and the like, with isopropyl acetate being preferred; and the second solvent may be pentane, cyclopentane, hexane, cyclohexane, methyl cyclohexane, heptanes, octane, nonane, decane, undecane, dodecane, ethanol, methanol, and the like, with n-heptane being preferred.

Preferably, in step (b), the temperature of the mixture is in the range of about 55° C. to about 65° C. In step (c), the temperature at which the mixture becomes supersaturated may be in the range of about 50° C. to about 55° C. The target temperature reached in step (d) may be in the range of about 31° C. to about 35° C., such as about 34° C. Preferably, in step (e), the homogenizing begins when the temperature of the mixture is about 0° C. to about 4° C. above the target temperature.

The invention also provides for crystallized particles of the compound of Formula (I) produced by the foregoing process. Preferably, the crystallized particles may have a surface area of about 0.80 to about 1.1 m$^2$/g, and more preferably, about 1.00 m$^2$/g. The Dv[50] of the crystallized particles may be about 10 to about 30 microns, preferably about 10 to about 20 microns.

Further, the invention provides a process for providing a depot injection comprising the compound of Formula (I) in crystal form

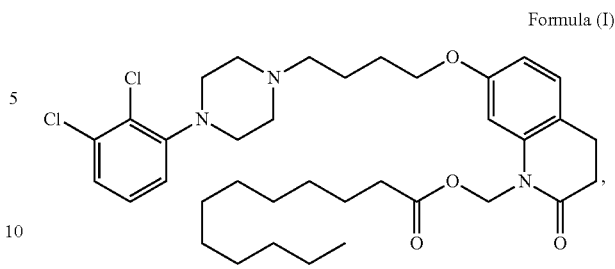

Formula (I)

the process comprising the steps of: (a) obtaining a drug solution by combining the compound of Formula (I) or a salt or solvate thereof with heated isopropyl acetate; (b) combining the drug solution with n-heptane to form a mixture with reduced solubility relative to the solubility of the drug solution; (c) cooling the mixture so that it becomes supersaturated; (d) cooling the mixture so that its temperature approaches a target temperature of about 34° C.; and (e) when the temperature of the mixture is within the range of about 5° C. above the target temperature, homogenizing the mixture to form crystallized particles of the compound of Formula (I) having a surface area of about 0.50 to about 3.3 m$^2$/g. Any one or more of steps (a) through (d) of the foregoing process may be performed under agitation. The foregoing process may further comprise the steps of (f) filtering the crystallized particles, (g) rinsing the crystallized particles, and (h) drying the crystallized particles.

Preferably, in step (b), the temperature of the mixture is in the range of about 55° C. to about 65° C. In step (c), the temperature at which the mixture becomes supersaturated may be in the range of about 50° C. to about 55° C. The target temperature reached in step (d) may be in the range of about 31° C. to about 35° C., such as about 34° C. Preferably, in step (e), the homogenizing begins when the temperature of the mixture is about 0° C. to about 4° C. above the target temperature.

The invention also provides for crystallized particles of the compound of Formula (I) produced by the foregoing process. Preferably, the crystallized particles may have a surface area of about 0.80 to about 1.1 m$^2$/g, and more preferably, about 1.00 m$^2$/g. The Dv[50] of the crystallized particles may be about 10 to about 30 microns, preferably about 10 to about 20 microns.

Still further, the invention provides a process for providing a depot injection comprising the compound of Formula (I) in crystal form

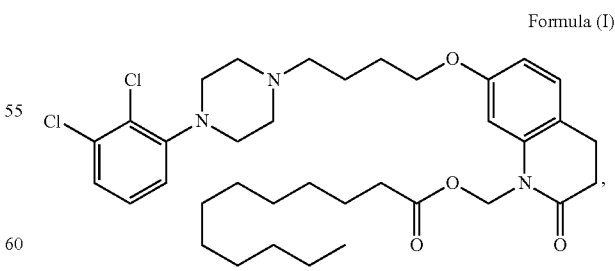

Formula (I)

the process comprising the steps of: (a) obtaining a drug solution by combining the compound of Formula (I) or a salt or solvate thereof with a first solvent; (b) combining the drug solution with a second solvent to form a mixture with reduced solubility relative to the solubility of the drug solution; (c) cooling the mixture so that it becomes supersaturated; (d) cooling the mixture so that its temperature approaches a target temperature; (e) when the temperature of the mixture is within the range of about 5° C. above the target temperature, homogenizing the mixture to form crystallized particles of the compound of Formula (I); (f) stopping homogenization, and re-dissolving the crystallized particles of the compound of Formula (I) by heating the mixture; (g) cooling the mixture so that its temperature approaches the target temperature; and (h) when the temperature of the mixture is within the range of about 5° C. above the target temperature, homogenizing the mixture to form crystallized particles of the compound of Formula (I) having a surface area of about 0.50 to about 3.3 m$^2$/g.

Steps (d), (e), and (f) of the foregoing process can be performed a second time (or three times, four times, etc.) prior to proceeding to step (g). For example, the process steps can be carried out in the order (a), (b), (c), (d), (e), (f), (d), (e), (f), (g), and (h); that is, steps (d) through (f) are performed twice in succession.

In the foregoing process, the first solvent may be ethyl acetate, propyl acetate, isopropyl acetate, butyl acetate, isobutyl acetate, tert-butyl acetate, acetone, and the like, with isopropyl acetate being preferred; and the second solvent may be pentane, cyclopentane, hexane, cyclohexane, methyl cyclohexane, heptanes, octane, nonane, decane, undecane, dodecane, ethanol, methanol, and the like, with n-heptane being preferred.

Any one or more of steps (a), (b), (c), (d), (e), (f), and (g) of the foregoing process may be performed under agitation. The foregoing process may further comprise the steps of (i) filtering the crystallized particles, (j) rinsing the crystallized particles, and (k) drying the crystallized particles.

Preferably, in step (b), the temperature of the mixture is in the range of about 55° C. to about 65° C. In step (c), the temperature at which the mixture becomes supersaturated may be in the range of about 50° C. to about 55° C. The target temperature reached in steps (d) and (g) may be in the range of about 31° C. to about 35° C., such as about 34° C.

Preferably, in steps (e) and (h), the homogenizing begins when the temperature of the mixture is about 0° C. to about 4° C. above the target temperature.

The invention also provides for crystallized particles of aripiprazole lauroxil produced by the foregoing process. Preferably, the crystallized particles may have a surface area of about 0.80 to about 1.1 m$^2$/g, and more preferably, about 1.00 m$^2$/g. The Dv[50] of the crystallized particles may be about 10 to about 30 microns, preferably about 10 to about 20 microns.

In alternative embodiments, the homogenizing of the processes described herein can be replaced with sonicating or the use of an ultrasound device.

The depot injection provided by any of the foregoing processes can provide for extended release of aripiprazole in vivo. Such extended release can occur, for example, over from a period of about one month to a period of about three months. Preferably, such extended release can occur, for example, over from a period of about one month to a period of about two months. The depot injection provided by any of the foregoing processes can be administered, for example, as a once-monthly injection, a once-every-two-months injection, or a once-every-three months injection.

DETAILED DESCRIPTION

Crystallization

Figure 1:
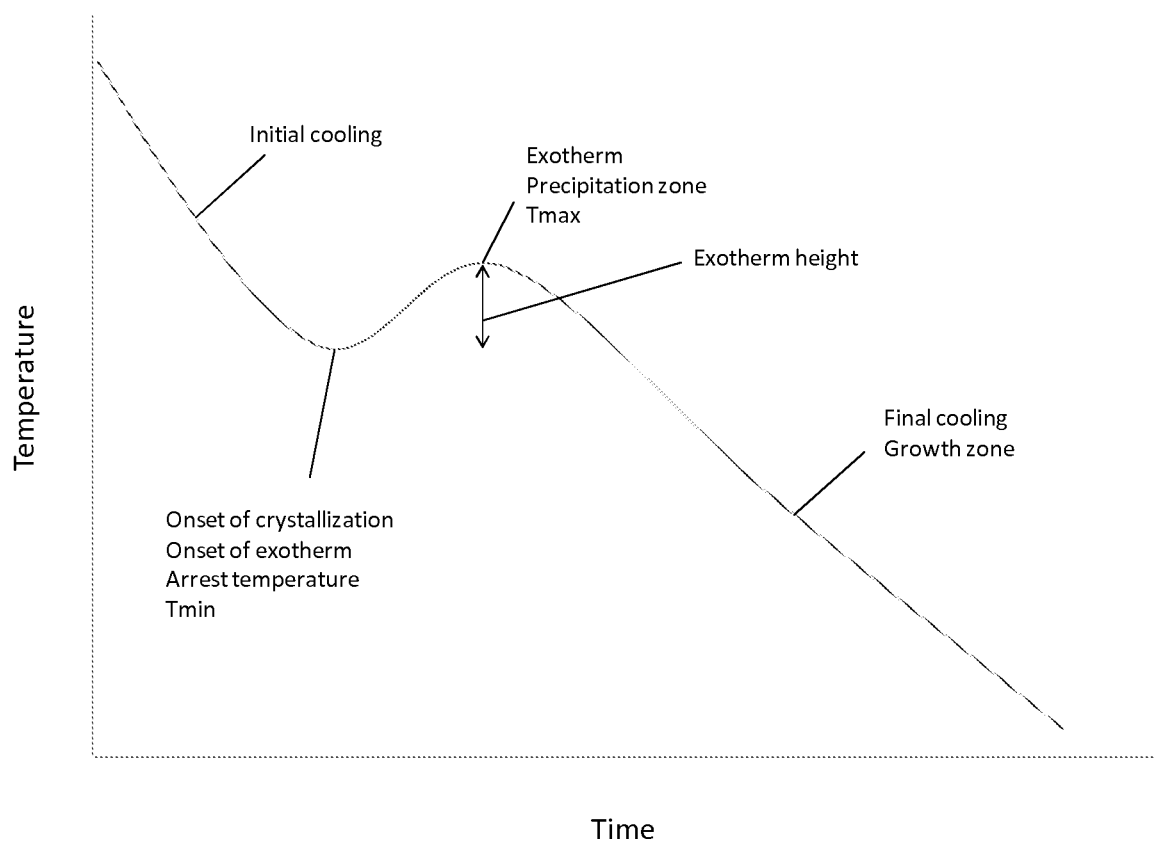
FIG. 1 depicts a typical cooling profile for the recrystallization process of the present invention.

Crystallization is a process of forming crystals through precipitation of solids from a solution, which occurs by variation of the solubility conditions of the solute in the solvent. The process is governed by both thermodynamic and kinetic factors, which can make it highly variable and difficult to control. These factors include component concentrations, impurity levels, mixing regime, vessel design, and cooling profile. All can have a major impact on the size, number, and shape of crystals produced.

Thermodynamically, crystallization is impossible below the theoretical solution solubility threshold (saturation). At values above this threshold, the solution is supersaturated (contains more solute than could be dissolved by the solvent under normal circumstances) and crystallization may proceed. Supersaturation is a fundamental factor in crystallization dynamics, where the level of supersaturation affects the crystallization rate and indicates that crystallization is under kinetic, rather than thermodynamic, control.

Crystallization consists of two major kinetic driven events: nucleation and crystal growth. Nucleation is the step where the solute molecules dispersed in the solvent start to gather into clusters (nuclei) that become stable under the current operating conditions. The crystal growth is the subsequent growth of the nuclei that succeed in producing stable crystals. Nucleation and growth continue to occur simultaneously while solution supersaturation exists.

Nucleation is the initiation of crystallization and is the sum effect of two categories, primary and secondary. Primary nucleation is the initial formation of nuclei where there are no other crystals present. This typically occurs through the influence/presence of other solids (i.e., walls of the crystallizer vessel and particles of any foreign substance). Secondary nucleation is the formation of nuclei attributable to the influence of already-existing crystals in the solution. Typically, this is a function of fluid shear and collisions of crystals and results in the formation of new nuclei. Several factors used to influence nucleation rate are use of seed crystals, equipment surface imperfections, and high shear homogenization.

The combination of solution supersaturation level and factors such as homogenization governs the nucleation rate, which in turn influences the crystal particle size and surface area. In general, a fast nucleation rate leads to smaller crystals, while a slow nucleation results in larger crystals. This is best understood through the concept of population balance. A fast nucleation rate creates a large number of small nuclei in a specified period, while a slow nucleation rate creates a lesser number in the same period. After the nuclei are generated, they then being to grow. Given a finite amount of mass available for growth, and assuming equivalent growth rates, the larger number population of nuclei will achieve a final particle size that is smaller (conversely larger surface area) than the lesser number population.

Aripiprazole Lauroxil

Aripiprazole lauroxil, an N-lauroyloxymethyl prodrug form of aripiprazole, has been developed for formulation into extended-release injectable formulations, such as for intramuscular injection. Aripiprazole lauroxil is a non-hygroscopic white crystalline solid with a melting point of 81.3 to 83.0° C., and it exists as a stable form, which has not been observed in any polymorphic modifications to date. The compound is insoluble in water (<4 ng/mL at room temperature) and shows highest room temperature solubility in the following organic solvents: THF (~400 mg/mL), dichloromethane (~500 mg/mL), and toluene (~300 mg/mL). The IUPAC name for aripiprazole lauroxil is (7-(4-(4-(2,3-dichlorophenyl)piperazin -1-yl)butoxy)-2-oxo-3,4-dihydro-2H-quinolin-1-yl)methyl dodecanoate, corresponding to the molecular formula $C_{36}H_{51}C_{12}N_3O_4$ and a molecular weight of 660.7. Aripiprazole lauroxil may also be referred to as N-lauroyloxymethyl aripiprazole. The chemical structure of aripiprazole lauroxil is as follows:

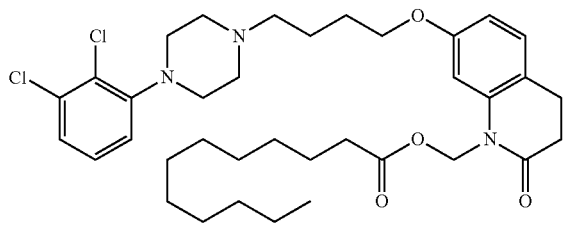 [SMILES: CCCCCCCCCCCC(=O)OCN1C(=O)CCc2ccc(OCCCCN3CCN(c4cccc(Cl)c4Cl)CC3)cc21]

and is also referred to herein as Formula (I).

Pre-processed aripiprazole lauroxil suitable for the recrystallization process described herein may be obtained, for example, by following the synthesis described in U.S. Pat. No. 8,431,576. This document is incorporated herein by reference in its entirety. Salts and solvates of aripiprazole lauroxil, which are disclosed and described in U.S. Pat. No. 8,431,576, are also suitable for the recrystallization process described herein.

Aripiprazole lauroxil undergoes hydrolysis to lauric acid, formaldehyde, and aripiprazole, which is an important antipsychotic used in the treatment of schizophrenia and other psychiatric conditions, such as bipolar disorder and major depressive disorder. Conversion of aripiprazole lauroxil to aripiprazole in vivo is governed by slow dissolution of the aripiprazole lauroxil drug crystals and subsequent enzyme-mediated cleavage to the N-hydroxymethyl aripiprazole intermediate, which spontaneously converts to aripiprazole.

The slow dissolution of the aripiprazole lauroxil drug crystals in vivo results in systemic exposure of aripiprazole over several weeks. The rate of aripiprazole lauroxil release is a function of the amount of exposed surface area, represented by particle size distribution (PSD) and shape/morphology of the drug crystals.

An extended release IM injection offers the potential for an improved safety profile and treatment compliance; therefore, it has the potential to provide more effective management of schizophrenia.

The present invention provides a process for providing a depot injection comprising aripiprazole lauroxil, i.e., the compound of Formula (I), in crystal form.

Formula (I)

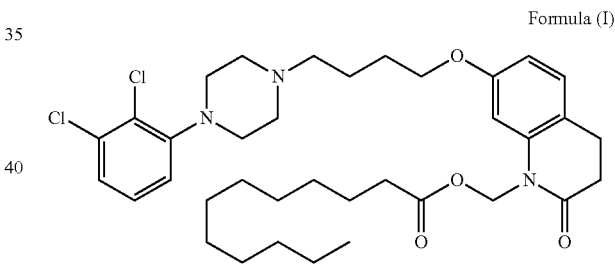

The process comprises the steps of: (a) obtaining a drug solution by combining the compound of Formula (I) or a salt or solvate thereof with a first solvent; (b) combining the drug solution with a second solvent to form a mixture with reduced solubility relative to the solubility of the drug solution; (c) cooling the mixture so that it becomes supersaturated; (d) cooling the mixture so that its temperature approaches a target temperature; and (e) when the temperature of the mixture is within the range of about 5° C. above the target temperature, homogenizing the mixture to form crystallized particles of the compound of Formula (I) having a surface area of about 0.50 to about 3.3 m²/g. Any one or more of steps (a) through (d) of the foregoing process may be performed under agitation. The foregoing process may further comprise the steps of (f) filtering the crystallized particles, (g) rinsing the crystallized particles, and (h) drying the crystallized particles.

In the foregoing process, the first solvent may be ethyl acetate, propyl acetate, isopropyl acetate, butyl acetate, isobutyl acetate, tert-butyl acetate, acetone, and the like, with isopropyl acetate being preferred; and the second solvent may be pentane, cyclopentane, hexane, cyclohexane, methyl cyclohexane, heptanes, octane, nonane, decane, undecane, dodecane, ethanol, methanol, and the like, with n-heptane being preferred.

Preferably, in step (b), the temperature of the mixture is in the range of about 55° C. to about 65° C. In step (c), the temperature at which the mixture becomes supersaturated may be in the range of about 50° C. to about 55° C. The target temperature reached in step (d) may be in the range of about 31° C. to about 35° C., such as about 34° C. Preferably, in step (e), the homogenizing begins when the temperature of the mixture is about 0° C. to about 4° C. above the target temperature.

The homogenizing in step (e) initializes and promotes crystallization, and allows for control of particle size and surface area. A suitable homogenization speed is from about 4800 to about 9600 rpm. The drying in step (h) can be conducted under nitrogen purge and vacuum.

The invention also provides for crystallized particles of the compound of Formula (I) produced by the foregoing process. Preferably, the crystallized particles may have a surface area of about 0.80 to about 1.1 m²/g, and more preferably, about 1.00 m²/g. The Dv[50] of the crystallized particles may be about 10 to about 30 microns, preferably about 10 to about 20 microns.

Further, the invention provides a process for providing a depot injection comprising the compound of Formula (I) in crystal form

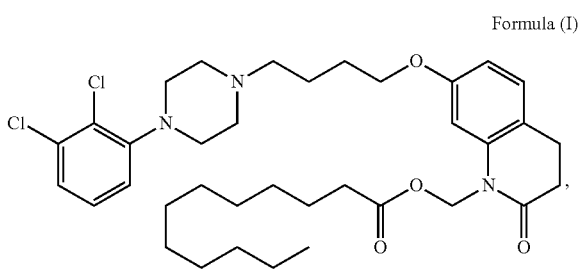 [SMILES: CCCCCCCCCCCC(=O)OCN1C(=O)CCc2ccc(OCCCCN3CCN(c4cccc(Cl)c4Cl)CC3)cc21]

Formula (I)

the process comprising the steps of: (a) obtaining a drug solution by combining the compound of Formula (I) or a salt or solvate thereof with heated isopropyl acetate; (b) combining the drug solution with n-heptane to form a mixture with reduced solubility relative to the solubility of the drug solution; (c) cooling the mixture so that it becomes supersaturated; (d) cooling the mixture so that its temperature approaches a target temperature of about 34° C.; and (e) when the temperature of the mixture is within the range of about 5° C. above the target temperature, homogenizing the mixture to form crystallized particles of the compound of Formula (I) having a surface area of about 0.50 to about 3.3 m²/g. Any one or more of steps (a) through (d) of the foregoing process may be performed under agitation. The foregoing process may further comprise the steps of (f) filtering the crystallized particles, (g) rinsing the crystallized particles, and (h) drying the crystallized particles.

Preferably, in step (b), the temperature of the mixture is in the range of about 55° C. to about 65° C. In step (c), the temperature at which the mixture becomes supersaturated may be in the range of about 50° C. to about 55° C. The target temperature reached in step (d) may be in the range of about 31° C. to about 35° C., such as about 34° C. Preferably, in step (e), the homogenizing begins when the temperature of the mixture is about 0° C. to about 4° C. above the target temperature.

The homogenizing in step (e) initializes and promotes crystallization, and allows for control of particle size and surface area. A suitable homogenization speed is from about 4800 to about 9600 rpm. The drying in step (h) can be conducted under nitrogen purge and vacuum.

The invention also provides for crystallized particles of the compound of Formula (I) produced by the foregoing process. Preferably, the crystallized particles may have a surface area of about 0.80 to about 1.1 m²/g, and more preferably, about 1.00 m²/g. The Dv[50] of the crystallized particles may be about 10 to about 30 microns, preferably about 10 to about 20 microns.

Still further, the invention provides a process for providing a depot injection comprising the compound of Formula (I) in crystal form

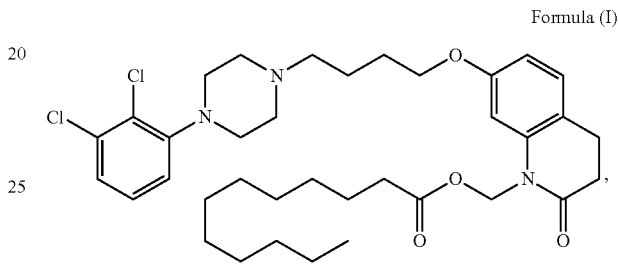

Formula (I)

the process comprising the steps of: (a) obtaining a drug solution by combining the compound of Formula (I) or a salt or solvate thereof with a first solvent; (b) combining the drug solution with a second solvent to form a mixture with reduced solubility relative to the solubility of the drug solution; (c) cooling the mixture so that it becomes supersaturated; (d) cooling the mixture so that its temperature approaches a target temperature; (e) when the temperature of the mixture is within the range of about 5° C. above the target temperature, homogenizing the mixture to form crystallized particles of the compound of Formula (I); (f) stopping homogenization, and re-dissolving the crystallized particles of the compound of Formula (I) by heating the mixture; (g) cooling the mixture so that its temperature approaches the target temperature; and (h) when the temperature of the mixture is within the range of about 5° C. above the target temperature, homogenizing the mixture to form crystallized particles of the compound of Formula (I) having a surface area of about 0.50 to about 3.3 m²/g.

Steps (d), (e), and (f) of the foregoing process can be performed a second time (or three times, four times, etc.) prior to proceeding to step (g). For example, the process steps can be carried out in the order (a), (b), (c), (d), (e), (f), (d), (e), (f), (g), and (h); that is, steps (d) through (f) are performed twice in succession.

In the foregoing process, the first solvent may be ethyl acetate, propyl acetate, isopropyl acetate, butyl acetate, isobutyl acetate, tert-butyl acetate, acetone, and the like, with isopropyl acetate being preferred; and the second solvent may be pentane, cyclopentane, hexane, cyclohexane, methyl cyclohexane, heptanes, octane, nonane, decane, undecane, dodecane, ethanol, methanol, and the like, with n-heptane being preferred.

Any one or more of steps (a), (b), (c), (d), (e), (f), and (g) of the foregoing process may be performed under agitation. The foregoing process may further comprise the steps of (i) filtering the crystallized particles, (j) rinsing the crystallized particles, and (k) drying the crystallized particles.

Preferably, in step (b), the temperature of the mixture is in the range of about 55° C. to about 65° C. In step (c), the temperature at which the mixture becomes supersaturated may be in the range of about 50° C. to about 55° C. The target temperature reached in steps (d) and (g) may be in the range of about 31° C. to about 35° C., such as about 34° C. Preferably, in steps (e) and (h), the homogenizing begins when the temperature of the mixture is about 0° C. to about 4° C. above the target temperature.

The homogenizing in steps (e) and (h) initializes and promotes crystallization, and allows for control of particle size and surface area. A suitable homogenization speed is from about 4800 to about 9600 rpm. The drying in step (k) can be conducted under nitrogen purge and vacuum.

The invention also provides for crystallized particles of the compound of Formula (I) produced by the foregoing process. Preferably, the crystallized particles may have a surface area of about 0.80 to about 1.1 m$^2$/g, and more preferably, about 1.00 m$^2$/g. The Dv[50] of the crystallized particles may be about 10 to about 30 microns, preferably about 10 to about 20 microns.

Each of the foregoing processes may use, instead of the compound of Formula (I), a salt or solvate thereof such as the salts or solvates of pre-processed aripiprazole lauroxil disclosed and described in U.S. Pat. No. 8,431,576.

Aripiprazole Cavoxil

Aripiprazole cavoxil, an N-hexanoyloxymethyl prodrug form of aripiprazole, has been developed for formulation into extended-release injectable formulations, such as for intramuscular injection. The IUPAC name for aripiprazole cavoxil is (7-(4-(4-(2,3-dichlorophenyl)piperazin-1-yl)butoxy)-2-oxo-3,4-dihydroquinolin-1(2H)-yl)methyl hexanoate, corresponding to the molecular formula $C_{30}H_{39}C_{12}N_3O_4$ and a molecular weight of 576.56. The chemical structure of aripiprazole cavoxil is as follows:

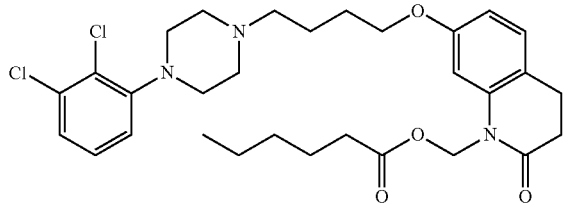 [SMILES: CCCCCC(=O)OCN1C(=O)CCc2ccc(OCCCCN3CCN(c4cccc(Cl)c4Cl)CC3)cc21]

and is also referred to herein as Formula (II). Aripiprazole cavoxil suitable for the processes described herein may be obtained, for example, by the synthesis methods described in U.S. Pat. No. 8,431,576. This document is incorporated herein by reference in its entirety. Salts and solvates of aripiprazole cavoxil, which are disclosed and described in U.S. Pat. No. 8,431,576, are also suitable for the processes described herein.

Process Equipment

The following process equipment was used to recrystallize aripiprazole lauroxil according to the present invention. Other suitable process equipment may be used, as would be well understood by one skilled in the art in light of present disclosure.

Drug dissolution vessel: To produce a 4.0 kg batch of recrystallized aripiprazole lauroxil, a single closed, jacketed, agitated 20 liter vessel was used to dissolve and transfer the drug through a sterilizing filter to the sterilized recrystallization vessel in a single step. A smaller pilot process (producing 1.75 kg of recrystallized aripiprazole lauroxil) used two small stock pots and hot plates to dissolve the drug, and multiple transfer steps to a 4 liter pressure vessel to sterile filter the solution into the recrystallization vessel. At both 4.0 kg and 1.75 kg scales, warm isopropyl acetate was used to dissolve the pre-processed drug crystals of aripiprazole lauroxil. As would be well understood by one of skill in the art, a "jacket" refers to heat transfer fluid and to the encased space around the vessel containing the heat transfer fluid that acts as a heat exchanger to cool or heat the inside of the vessel, and a "glycol jacket" is a jacket where the heat transfer fluid is glycol or a mixture of water and glycol. The glycol jacket temperature affects primary cooling, which transitions the system into a meta-stable zone where crystallization of aripiprazole lauroxil can be initiated with homogenization.

Drug solution filter: The drug solution filter used for both scales was Milliport Aervent OptiSeal Cartridge, PTFE Hydrophobic, LAGR04TP6 (112-00783).

Filter heat tape: The filter heat tape used for both scales was Fiberglass Cloth Heating Tape with Glas-Col PowrTrol Controller (10 amps/120 volts).

Recrystallization vessel: The recrystallization vessel used for both scales was a DCI 24-Liter Cone Shaped (16" upper ID/23° angle) Stainless Steel Jacketed Vessel (DCI Serial #: J52884) with a 3.75" Radial Lower Impeller, 3.75" Axial Upper Impeller on an angled (non-vertical) agitator.

Homogenizer: The homogenizer used for both scales was a Kinematica Polytron PT-D 50-6 F/G (installed in the recrystallization vessel) with 50 mm Stator Diameter and 45 mm Rotor Diameter.

Sonicator: An exemplary sonicator suitable for use with the process of the present invention is Transsonic T310 from Lab-Line Instruments Inc.

Dryer: The dryer used in the 4.0 kg scale process was a closed, agitated, 15" self-discharging vacuum filter dryer (Powder Systems Limited; PSL). The 1.75 kg scale process used two 8" static vacuum filter dryers that required manual aseptic stirring of the recrystallized drug crystals prior to drying and discharge. The mode of drying was the same at both scales, namely, the recrystallized drug crystals were dried under vacuum at room temperature with a dry gas purge to facilitate removal of processing solvents to acceptably low levels.

Filtrate vessel: The filtrate vessel used in both scales was a DCI 10-gallon Stainless Steel Jacketed Vessel (DCI Serial #: JS2060).

Recrystallization Process

The recrystallization process of the present invention can produce crystallized particles of aripiprazole lauroxil having a surface area of about 0.50 to about 3.3 m$^2$/g, preferably about 0.80 to about 1.1 m$^2$/g, more preferably about 1.00 m$^2$/g. The Dv[50] of the crystallized particles may be about 10 to about 30 microns, preferably about 10 to about 20 microns.

Recrystallized aripiprazole lauroxil can be produced through the following procedure:

Drug Dissolution: Dissolve pre-processed aripiprazole lauroxil or a salt or solvate thereof in a first solvent such as isopropyl acetate or another suitable first solvent as described herein, and sterile filter the result into a recrystallization vessel.

Crystallization: Mix the drug solution (aripiprazole lauroxil dissolved in, e.g., isopropyl acetate) and a second solvent such as heptane or another suitable second solvent as described herein and then cool at a controlled rate; initiate homogenization at a target temperature to induce crystallization.

Collection: Transfer contents of recrystallization vessel and filter crystals from the solvent in a dryer.

Rinsing: Use a fresh portion of the second solvent to recover any crystals remaining in the recrystallization vessel and remove gross residual first solvent from the crystal surface. Rinsing can also remove residual amounts of acetonitrile, which may have been present in the pre-processed aripiprazole lauroxil.

Drying: Use vacuum drying to reduce levels of both the first and second solvents.

The first solvent may be ethyl acetate, propyl acetate, isopropyl acetate, butyl acetate, isobutyl acetate, tert-butyl acetate, acetone, or another suitable solvent as would be well understood by one skilled in the art in light of the present disclosure, or mixtures of the foregoing solvents. Isopropyl acetate is a preferred first solvent.

The second solvent may be pentane, cyclopentane, hexane, cyclohexane, methyl cyclohexane, heptanes, octane, nonane, decane, undecane, dodecane, ethanol, methanol, or another suitable solvent as would be well understood by one skilled in the art in light of the present disclosure, or mixtures of the foregoing solvents. N-heptane is a preferred second solvent.

A preferred selection and ratio of first solvent and second solvent is isopropyl acetate and heptanes, in a ratio of 1:2 (v/v).

When the drug solution of aripiprazole lauroxil in a first solvent (such as isopropyl acetate) is combined with the second solvent (such as heptane), this forms a mixture with reduced solubility relative to the solubility of the drug solution. The drug solution and the second solvent are preferably combined at a temperature of from about 55° C. to about 65° C., and then the mixture is cooled at a specified rate, such as 1.5° C. per minute, so that the mixture becomes supersaturated. The temperature at which the mixture becomes supersaturated may be in the range of about 50° C. to about 55° C.

Then the mixture is cooled so that its temperature approaches a target temperature. This target temperature may be in the range of about 31° C. to about 35° C., such as about 34° C. When the temperature of the mixture is within the range of about 0° C. to about 4° C. above the target temperature, homogenization of the mixture is initiated. A suitable speed for homogenization is from about 4800 to about 9600 rpm.

Drug dissolution, combining the drug solution and the second solvent, cooling the mixture of the drug solution and the second solvent, cooling the mixture once it has become supersaturated, homogenizing the mixture, and re-dissolving the crystallized particles of aripiprazole lauroxil by heating the mixture can each be performed under agitation. The agitation may be carried out with an agitator such as an overhead stirrer. The agitator helps to maintain a uniform crystal suspension and control over the temperature.

Suitable salts and solvates of pre-processed aripiprazole lauroxil that can be obtained, synthesized, and used with the present invention include those disclosed in U.S. Pat. No. 8,431,576.

Formulations

The recrystallized aripiprazole lauroxil prepared according to the methods disclosed herein can be suspended in injection vehicles to produce injectable compositions suitable, for example, for IM administration. Such vehicles include a phosphate-buffered saline injection vehicle comprising sorbitan monolaurate in an amount of approximately 0.37% by weight relative to the weight of the injectable composition; polysorbate 20 in an amount of approximately 0.15% by weight relative to the weight of the injectable composition; and an aqueous carrier. The recrystallized aripiprazole lauroxil prepared according to the methods disclosed herein can also be incorporated into other vehicles and formulations, such as those disclosed in U.S. Patent Application Publication No. 2012/0238552.

The following is the formulation of an exemplary depot injection composition comprising recrystallized aripiprazole lauroxil prepared according to the methods disclosed herein:

| Formulation | Amount Per Dose (% w/w) |
| --- | --- |
| Recrystallized Aripiprazole Lauroxil Drug Substance | 26.6 |
| Sorbitan Monolaurate | 0.37 |
| Polysorbate 20 | 0.15 |
| Sodium Chloride | 0.59 |
| CMC | NA |
| Sodium Phosphate Dibasic Anhydrous | 0.06 |
| Sodium Dihydrogen Phosphate Monobasic Dihydrate | 0.05 |
| Water for Injection | QS to 100 |

Relation of Particle Size and Release Rate

Particle size of the aripiprazole lauroxil produced from the recrystallization process of the present invention was shown to relate to release rate in animal studies and thus required controlling to within an acceptable range. The particle size distribution (PSD) of recrystallized aripiprazole lauroxil produced according to the process disclosed herein can be measured, for example, using a light scattering particle size analyzer such as those available from HORIBA or Beckman-Coulter, or by other suitable instruments and methods as would be well understood by one skilled in the art in light of the present disclosure.

As used herein, "Dv[50]" refers to the 50th percentile of the particle size distribution, which is interchangeable with median diameter or the average particle diameter by volume. As used herein, "Dv[10]" refers to the 10th percentile of the particle size distribution, "Dv[90]" refers to the 90th percentile of the particle size distribution, and "Dv[X]" refers to the Xth percentile of the particle size distribution.

An acceptable Dv[50] range of particles of aripiprazole lauroxil produced from the recrystallization process of the present invention is 10-30 microns, with a Dv[50] of 10-20 microns being preferred.

The relation of particle size and release rate is further explained in the studies and examples further below.

Relation of Surface Area and Release Rate

Drug release was found to be proportional to the surface area of aripiprazole lauroxil produced from the recrystallization process of the present invention.

The surface area of recrystallized aripiprazole lauroxil particles can be measured, for example, using an accelerated surface area and porosimetry analyzer, or by other suitable instruments and methods as would be well understood by one skilled in the art in light of the present disclosure.

An acceptable surface area range for particles of aripiprazole lauroxil produced from the recrystallization process of the present invention is from about 0.50 to about 3.3 m$^2$/g. A surface area range of 0.80 to about 1.1 m$^2$/g is preferred, and a surface area of about 1.0 m$^2$/g is more preferred.

The relation of surface area and release rate is further explained in the studies and examples further below.

Cooling Profile

FIG. 1 depicts a typical cooling profile for the recrystallization process of the present invention. Cooling of a mixture containing aripiprazole lauroxil, first solvent, and second solvent causes the temperature of the mixture to decrease, and the mixture becomes supersaturated. Aripiprazole lauroxil precipitates, causing an increase in temperature of the system. This is followed by further cooling of the system. As used herein, the term "exotherm" refers to the increase in temperature of the system due to precipitation of the drug. The "precipitation zone," in which the exotherm occurs, begins when the temperature starts to increase and covers the entire period during which aripiprazole lauroxil is precipitating or crystallizing. The "arrest temperature" or target temperature is the temperature at which no further decrease in temperature of the system is observed and the start (or onset) of crystallization occurs. Homogenization is preferably initiated when the temperature of the supersaturated mixture of aripiprazole lauroxil is a few degrees above the arrest or target temperature. Homogenization promotes crystallization and allows for control of particle size and surface area. "Tmin" indicates the initial temperature increase due to exothermic heating from the major crystallization event. Tmin, which defines both the "onset of crystallization" and the "onset of exotherm," is directly correlated with particle size and surface area of the recrystallized particles of aripiprazole lauroxil. "Tmax," or the exotherm maximum temperature, denotes the completion of significant exothermic heating from the major crystallization event. Following the major crystallization event, the slurry is further cooled in the "final cooling" stage (growth zone). "$Tmin_2$" is the temperature equal to Tmin that occurs upon cooling of the system following the exotherm associated with crystallization.

STUDIES AND EXAMPLES

Homogenization

Figure 2:
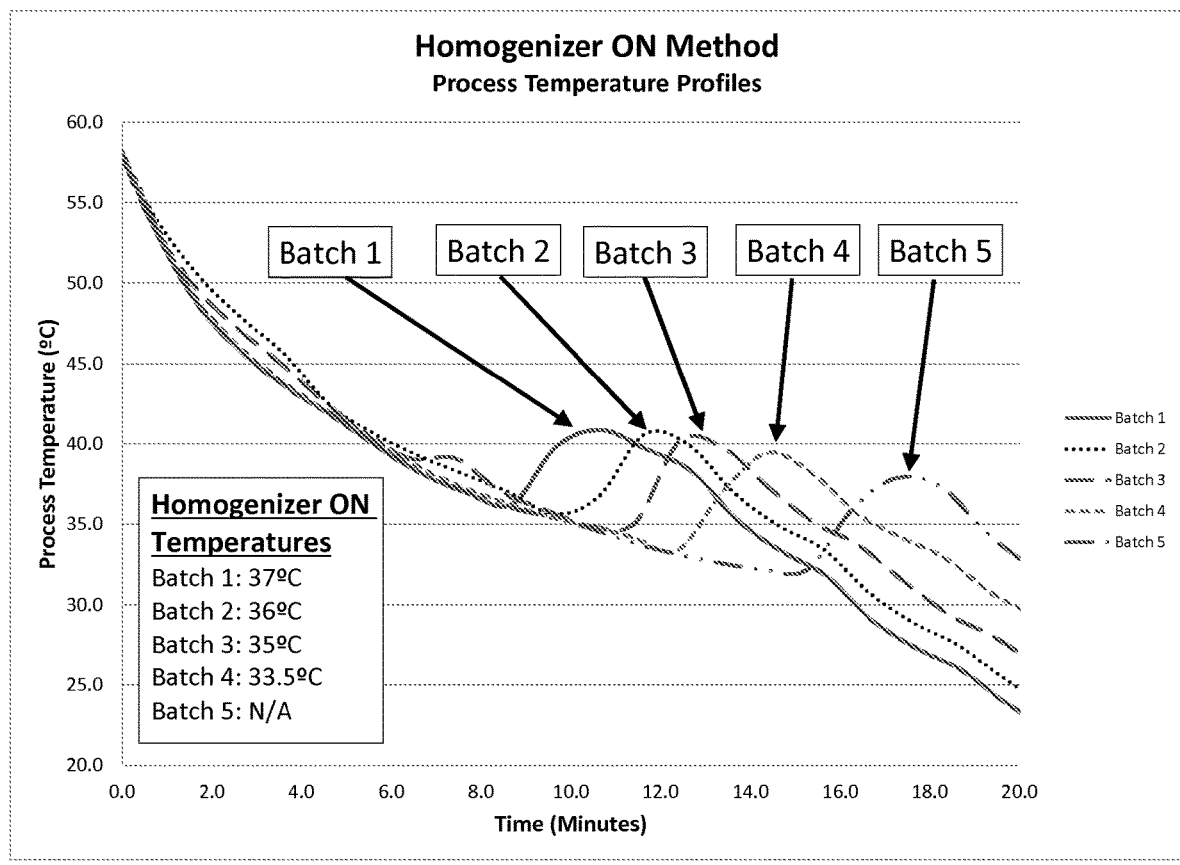
FIG. 2 is a graph showing that homogenizer initiation induced crystallization of aripiprazole lauroxil at a target temperature.

As illustrated in FIG. 2, homogenizer initiation induces crystallization at a target temperature. The results of five crystallization tests at the 1.75 kg scale are reflected in FIG. 2. All of the crystallization tests had the same cooling rate, but each used a different homogenizer initiation temperatures and resulted in different exotherm onset temperatures and, as a result, different crystal sizes. In four of the tests, the homogenizer was turned on at the respective temperature specified in the plot, and crystallization was induced soon after the initiation of homogenization. The Batch 5 test shows the point when spontaneous crystallization occurred, when no homogenization was used at the given cooling rate.

Impact of Homogenizer Initiation Temperature on Crystal Size (Single Factor Screening)

The objective of this study was to screen the impact of homogenization initiation temperature ("Homogenizer ON") on the surface area and particle size of recrystallized aripiprazole lauroxil, as well as the crystallization induction time and exotherm onset temperature. The study evaluated homogenizer initiation temperature at three values (35, 36, and 37° C.) while the following parameters were held constant: Homogenizer speed—75% (120 Hz/7200 rpm); Vessel agitation speed—375 rpm; Vessel jacket glycol temperature set-point—30° C. (this parameter dictates the solution primary cooling rate).

Table 1 summarizes several tests at the 4 kg scale used to evaluate the effect of homogenizer initiation temperature (Homogenizer ON) on in-process crystal particle size. By "exotherm onset temperature" is meant the temperature at which dissolved aripiprazole lauroxil begins to recrystallize.

TABLE 1

Effect of Homogenizer ON Temperature (4 kg Scale)

| Test | Homogenizer ON Temperature (° C.) | Exotherm Onset Temperature (° C.) | PSD (Micron) | | |
|---|---|---|---|---|---|
| | | | Dv[10] | Dv[50] | Dv[90] |
| B1 | 37 | 35.8 | 6 | 21 | 37 |
| B2 | 36 | 35.4 | 5 | 17 | 31 |
| B3 | 35 | 34.7 | 4 | 14 | 29 |

Figure 3:
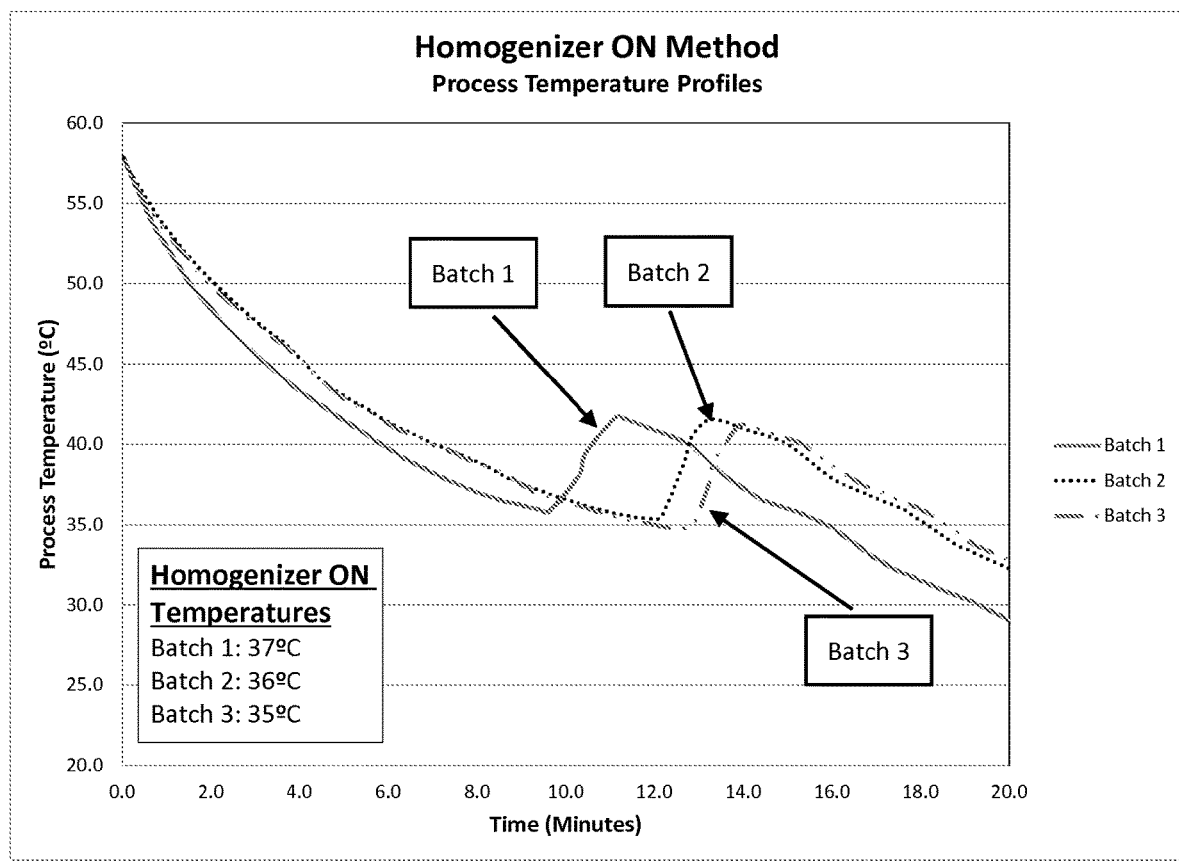
FIG. 3 depicts temperature profiles for recrystallization tests at the 4 kg scale.

FIG. 3 shows the temperature profiles for the tests at the 4 kg scale. The plots showed that crystallization (observed by the exotherm) occurred shortly after homogenizer initiation, as was previously demonstrated at the 1.75 kg scale (FIG. 2).

Impact of Crystallization Variables on Particle Size and Surface Area (Multi-Factor Screening)

The objective of this study was to characterize the impact of homogenizer initiation temperature and homogenizer speed on surface area and particle size as well as the crystallization induction time and exotherm onset temperature. The study evaluated the two factors of homogenizer initiation temperature and homogenizer speed, both factors being studied at three levels. The study used a full factorial experimental design with a center-point resulting in ten (10) crystallizations. The jacket glycol temperature set-point was adjusted as a function of the homogenizer initiation temperature. The intent was to maintain a heat transfer temperature gradient (at crystallization) between 5-7° C. This value is defined as the difference between the jacket glycol temperature set-point and homogenizer initiation temperature.

Table 2 summarizes tests from the multi-factor screening study used to evaluate the combinatory effect of homogenizer initiation temperature (Homogenizer ON) and homogenizer speed on in-process crystal surface area and particle size. The jacket glycol temperature set-point was varied to maintain the gradient in a range of 5-7° C. in order to minimize the under-cooling temperature delta.

Figure 4:
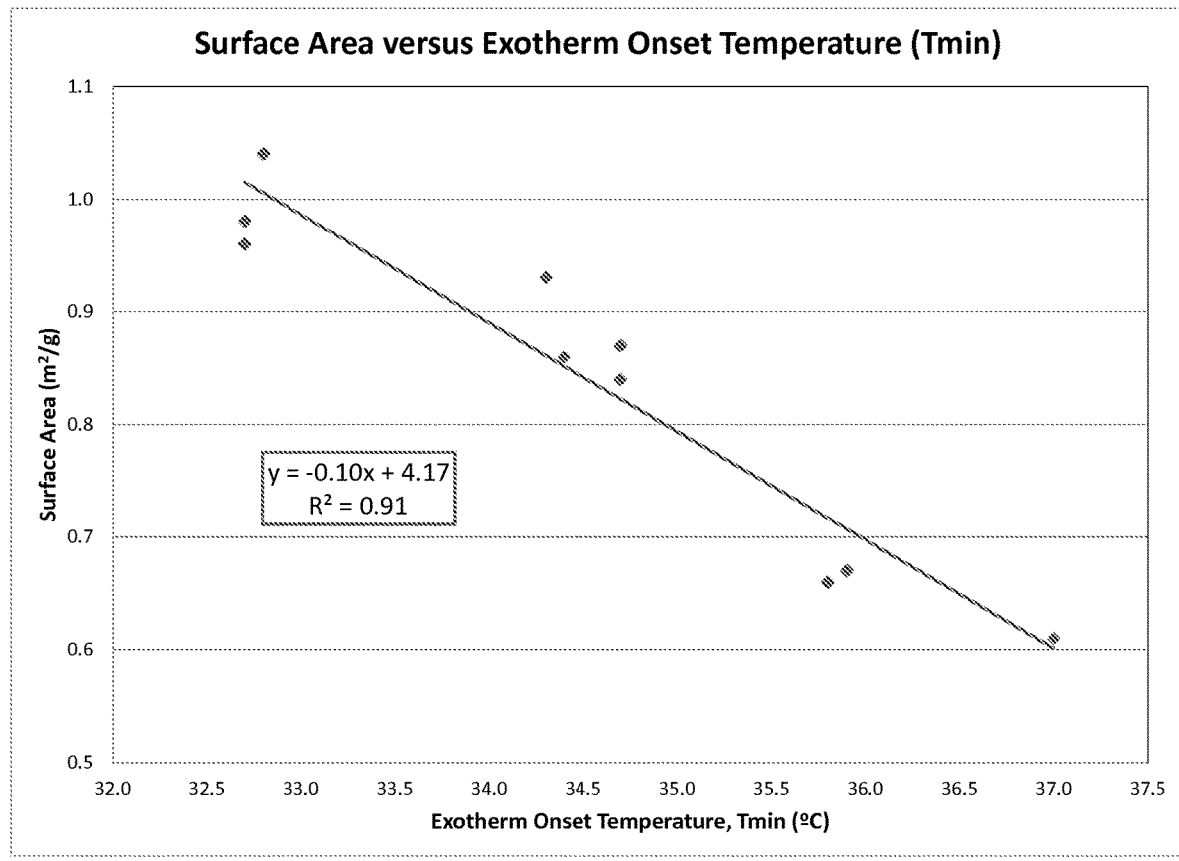
FIG. 4 is a graph showing the relationship between surface area of particles of recrystallized aripiprazole lauroxil and exotherm onset temperature.
Figure 5:
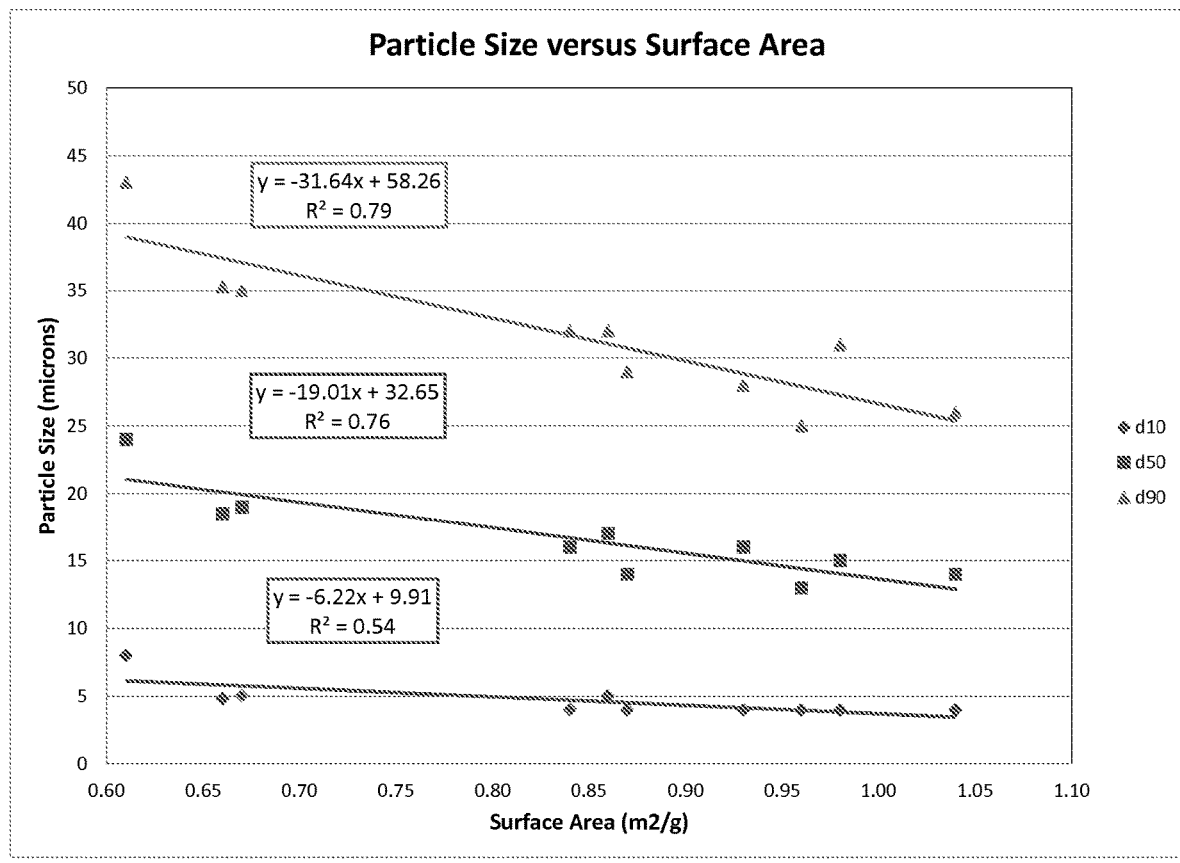
FIG. 5 is a graph showing the relationship between particle size and surface area.

FIG. 4 and FIG. 5 present plots of surface area versus exotherm onset temperature and particle size versus surface area. The plots demonstrate that the strong relationship observed between these attributes at the 1.75 kg scale continued to be present at the 4 kg scale.

TABLE 2

Effect of Crystallization Parameters (Multi-factor Screening)

| Test | Pattern | Glycol Jacket Temp. (° C.) | Homg. Setting (%) | Homg. ON Temp. (° C.) | Exotherm Onset Temp. (° C.) | Under-cooling Temp. Delta (° C.) | Heat Transfer Temp. Gradient (° C.) | Surface Area ($m^2$/g) | PSD (Micron) Dv[10] | Dv[50] | Dv[90] |
|---|---|---|---|---|---|---|---|---|---|---|---|
| C1 | 31 | 30 | 50 | 37 | 35.8 | 1.2 | 7 | 0.66 | 5 | 19 | 35 |
| C2 | 32 | 30 | 75 | 37 | 35.9 | 1.1 | 7 | 0.67 | 5 | 19 | 35 |
| C3 | 33 | 30 | 100 | 37 | 37.0 | 0 | 7 | 0.61 | 8 | 24 | 43 |
| C4 | 11 | 27 | 50 | 33 | 32.7 | 0.3 | 6 | 0.98 | 4 | 15 | 31 |
| C5 | 0 | 30 | 75 | 35 | 34.4 | 0.6 | 5 | 0.86 | 5 | 17 | 32 |
| C6 | 13 | 28 | 100 | 33 | 32.7 | 0.3 | 5 | 0.96 | 4 | 13 | 25 |
| C7 | 22 | 30 | 75 | 35 | 34.7 | 0.3 | 5 | 0.87 | 4 | 14 | 29 |
| C8 | 21 | 30 | 50 | 35 | 34.7 | 0.3 | 5 | 0.84 | 4 | 16 | 32 |
| C9 | 23 | 30 | 100 | 34.5 | 34.3 | 0.2 | 4.5 | 0.93 | 4 | 16 | 28 |
| C10 | 12 | 27 | 75 | 33 | 32.8 | 0.2 | 6 | 1.04 | 4 | 14 | 26 |

Impact of Crystallization Variables on Particle Size and Surface Area (Multi-Factor DOE)

The objective of this study was to characterize the impact of homogenizer initiation temperature and homogenizer speed on surface area and particle size as well as the crystallization induction time and exotherm onset temperature. This study was equivalent to the study Impact of crystallization variables on particle size and surface area (multi-factor screening) above, but executed in a different process train. This study evaluated the two factors of homogenizer initiation temperature and homogenizer speed, each at three levels. The study used a full factorial experimental design resulting in nine (9) crystallizations. The jacket glycol temperature set-point was adjusted as a function of the homogenizer initiation temperature. The intent was to maintain a heat transfer temperature gradient (at crystallization) of 6° C. This value is defined as the difference between the jacket glycol temperature set-point and homogenizer initiation temperature.

Table 3 summarizes tests from the multi-factor DOE (design of experiments) study used to evaluate the combinatory effect of homogenizer initiation temperature (Homogenizer ON) and homogenizer speed on in-process crystal surface area and particle size. The jacket glycol temperature set-point was varied to maintain the gradient at a specified 6° C. in order to minimize the under-cooling temperature delta. The study showed that the impact of Homogenizer ON temperature and the impact of homogenizer speed parameters were both statistically significant.

Impact of Crystallization Variables on Particle Size and Surface Area (Multi-Factor Augmented DOE)

The objective of this study was to characterize the impact of homogenizer initiation temperature, homogenizer speed, and heat transfer temperature gradient (at crystallization) on surface area and particle size as well as the crystallization induction time and exotherm onset temperature. This study augmented the foregoing multi-factor DOE study by incorporating the additional parameter of heat transfer temperature gradient. The study evaluated the three factors of homogenizer initiation temperature, homogenizer speed, and heat transfer temperature gradient (at crystallization), each at three levels. The study used a central composite experimental design with center-point replicates resulting in seventeen (17) crystallizations. The jacket glycol temperature set-point was adjusted as a function of the homogenizer initiation temperature in order to set the heat transfer temperature gradient (at crystallization). This value is defined as the difference between the jacket glycol temperature set-point and homogenizer initiation temperature.

Table 4 summarizes tests from the augmented multi-factor DOE study used to evaluate the combinatory effect of homogenizer initiation temperature (Homogenizer ON), homogenizer speed, and heat transfer temperature gradient on in-process crystal surface area, particle size, and exotherm onset temperature. This DOE augmented the immediately previous experimental design by including heat transfer temperature gradient as a factor. Again, the jacket

TABLE 3

Effect of Crystallization Parameters (Multi-factor DOE)

| Test | Pattern | Glycol Jacket Temp. (° C.) | Homg. Setting (%) | Homg. ON Temp. (° C.) | Exotherm Onset Temp. (° C.) | Under-cooling Temp. Delta (° C.) | Heat Transfer Temp. Gradient (° C.) | Surface Area ($m^2$/g) | PSD (Micron) Dv[10] | Dv[50] | Dv[90] |
|---|---|---|---|---|---|---|---|---|---|---|---|
| D1 | 13 | 26 | 100 | 32 | 31.7 | 0.3 | 6 | 1.07 | 3 | 13 | 23 |
| D2 | 12 | 26 | 75 | 32 | 31.7 | 0.3 | 6 | 1.02 | 4 | 14 | 26 |
| D3 | 23 | 28 | 100 | 34 | 33.7 | 0.3 | 6 | 0.91 | 4 | 16 | 28 |
| D4 | 11 | 26 | 50 | 32 | 31.6 | 0.4 | 6 | 1.02 | 3 | 14 | 27 |
| D5 | 21 | 28 | 50 | 34 | 33.5 | 0.5 | 6 | 0.88 | 4 | 17 | 32 |
| D6 | 32 | 30 | 75 | 36 | 35.4 | 0.6 | 6 | 0.73 | 5 | 19 | 34 |
| D7 | 33 | 30 | 100 | 36 | 35.5 | 0.5 | 6 | 0.77 | 6 | 19 | 34 |
| D8 | 31 | 30 | 50 | 36 | 35.2 | 0.8 | 6 | 0.69 | 4 | 19 | 35 |
| D9 | 22 | 28 | 75 | 34 | 33.6 | 0.4 | 6 | 0.89 | 3 | 13 | 25 | glycol temperature set-point was varied to maintain the gradient at specified values of 4, 6, and 8° C.

FIGS. 6, 7, 8, 9, and 10 show several models built from the results. Table 5 summarizes the findings from these models. All models were statistically significant based on ANOVA (p-values<0.05) and demonstrate no Lack of Fit.

Figure 11:
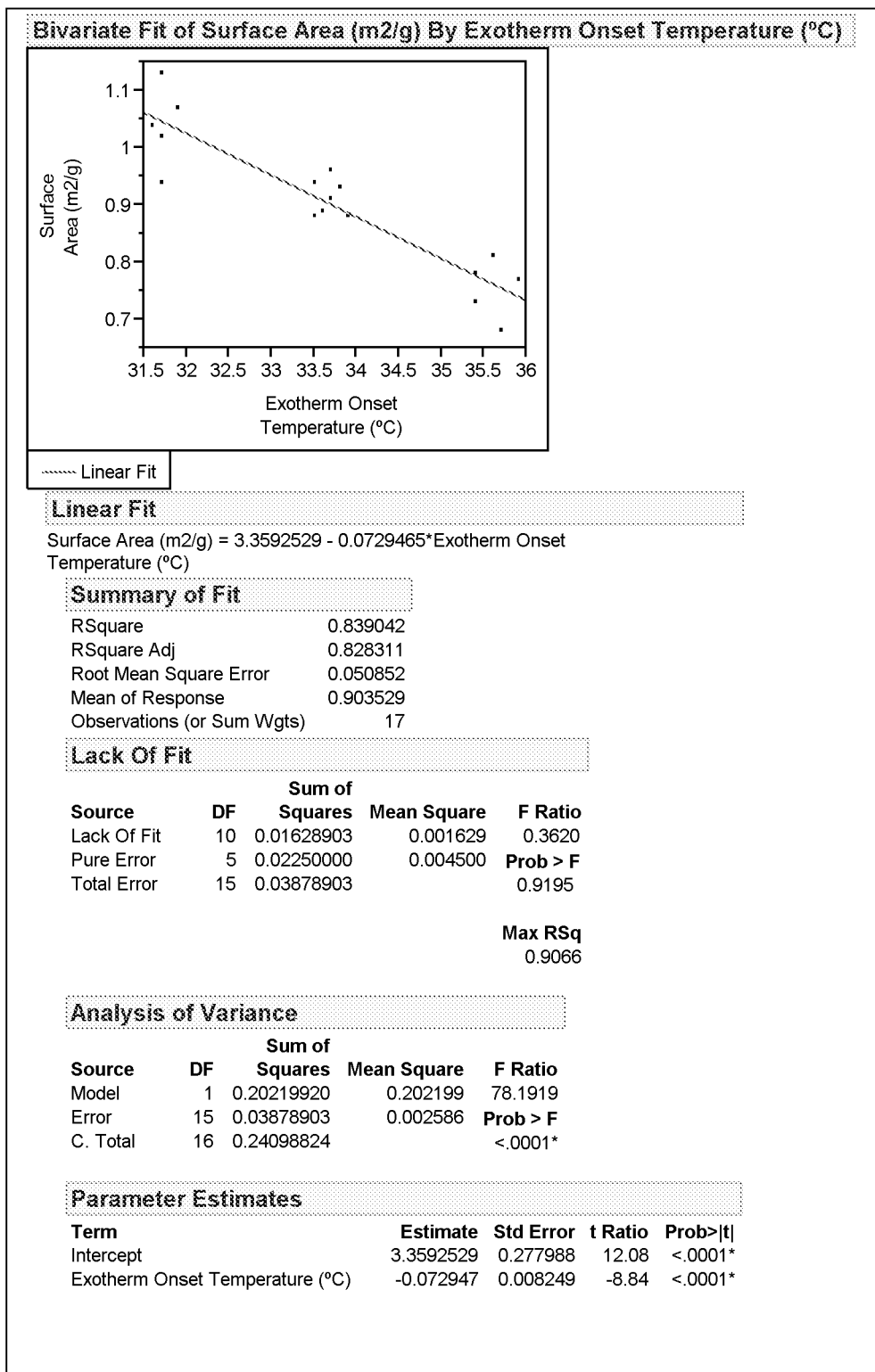
FIG. 11 shows the relationship between surface area of particles of recrystallized aripiprazole lauroxil and exotherm onset temperature as revealed by an augmented multi-factor DOE study.

FIG. 11 shows the relationship between surface area and exotherm onset temperature. Linear regression analysis demonstrated statistical significance per ANOVA (p-values<0.05). The excellent relationship of surface area to exotherm onset temperature was advantageous because it provided an in-process measurement of crystallization progression or performance. Advantageously, in the event that the exotherm onset temperature fell outside the predicted or target range during a crystallization, the run could be discontinued, the material re-heated, and the crystallization repeated.

type (spontaneous versus induced) on the crystallization induction time and exotherm onset temperature. The study used a designed experiment (central composite design) consisting of 10 runs that incorporated two factors at three levels: Vessel Jacket Temperature (3° C., 16.5° C., 30° C.); and Homogenizer Speed (0%, 37.5%, 75%).

Table 6 summarizes tests from the multi-factor DOE (central composite design) consisting of 10 runs that incorporated the two factors at three levels: Vessel Jacket Temperature (3° C., 16.5° C., 30° C.); and Homogenizer Speed (0%, 37.5%, 75%). Each run that used a 0% homogenizer speed (no homogenization) was cooled until it spontaneously crystallized. In the runs that used homogenizer speeds of 37.5% and 75%, the homogenizer was turned on when the process temperature cooled to 53.6° C. (This temperature represents the solubility limit of the process solution below which the solution enters a meta-stable state.) The solution

TABLE 4

Effect of Crystallization Parameters (Multi-factor Augmented DOE)

| Test ID | Pattern | Homg. Setting (%) | Homg. ON Temp. (° C.) | Glycol Jacket Temp. (° C.) | Heat Transfer Temp. Gradient (° C.) | Under-cooling Temp. Delta (° C.) | Exotherm Onset Temp. (° C.) | Surface Area (m²/g) | PSD (Micron) Dv[10] | Dv[50] | Dv[90] |
|---|---|---|---|---|---|---|---|---|---|---|---|
| E1 | 0a0 | 75 | 32 | 26 | 6 | 0.3 | 31.7 | 1.02 | 4 | 14 | 26 |
| E2 | A00 | 100 | 34 | 28 | 6 | 0.3 | 33.7 | 0.91 | 4 | 16 | 28 |
| E3 | a00 | 50 | 34 | 28 | 6 | 0.5 | 33.5 | 0.88 | 4 | 17 | 32 |
| E4 | 0A0 | 75 | 36 | 30 | 6 | 0.6 | 35.4 | 0.73 | 5 | 19 | 34 |
| E5 | 0 | 75 | 34 | 28 | 6 | 0.4 | 33.6 | 0.89 | 3 | 13 | 25 |
| E6 | 00a | 75 | 34 | 30 | 4 | 0.1 | 33.9 | 0.88 | 5 | 18 | 33 |
| E7 | −+− | 50 | 36 | 32 | 4 | 0.3 | 35.7 | 0.68 | 6 | 24 | 43 |
| E8 | −−+ | 50 | 32 | 24 | 8 | 0.4 | 31.6 | 1.04 | 4 | 16 | 33 |
| E9 | +++ | 100 | 36 | 28 | 8 | 0.4 | 35.6 | 0.81 | 6 | 20 | 33 |
| E10 | 00A | 75 | 34 | 26 | 8 | 0.5 | 33.5 | 0.94 | 5 | 17 | 32 |
| E11 | 0 | 75 | 34 | 28 | 6 | 0.2 | 33.8 | 0.93 | 5 | 17 | 30 |
| E12 | −−− | 50 | 32 | 28 | 4 | 0.3 | 31.7 | 0.94 | 4 | 18 | 36 |
| E13 | +−+ | 100 | 32 | 24 | 8 | 0.3 | 31.7 | 1.13 | 4 | 16 | 30 |
| E14 | ++− | 100 | 36 | 32 | 4 | 0.1 | 35.9 | 0.77 | 6 | 22 | 38 |
| E15 | −++ | 50 | 36 | 28 | 8 | 0.6 | 35.4 | 0.78 | 6 | 23 | 42 |
| E16 | 0 | 75 | 34 | 28 | 6 | 0.3 | 33.7 | 0.96 | 5 | 18 | 35 |
| E17 | +−− | 100 | 32 | 28 | 4 | 0.1 | 31.9 | 1.07 | 4 | 15 | 28 |

TABLE 5

Summary of Multi-factor Augmented DOE Models

Figure 6:
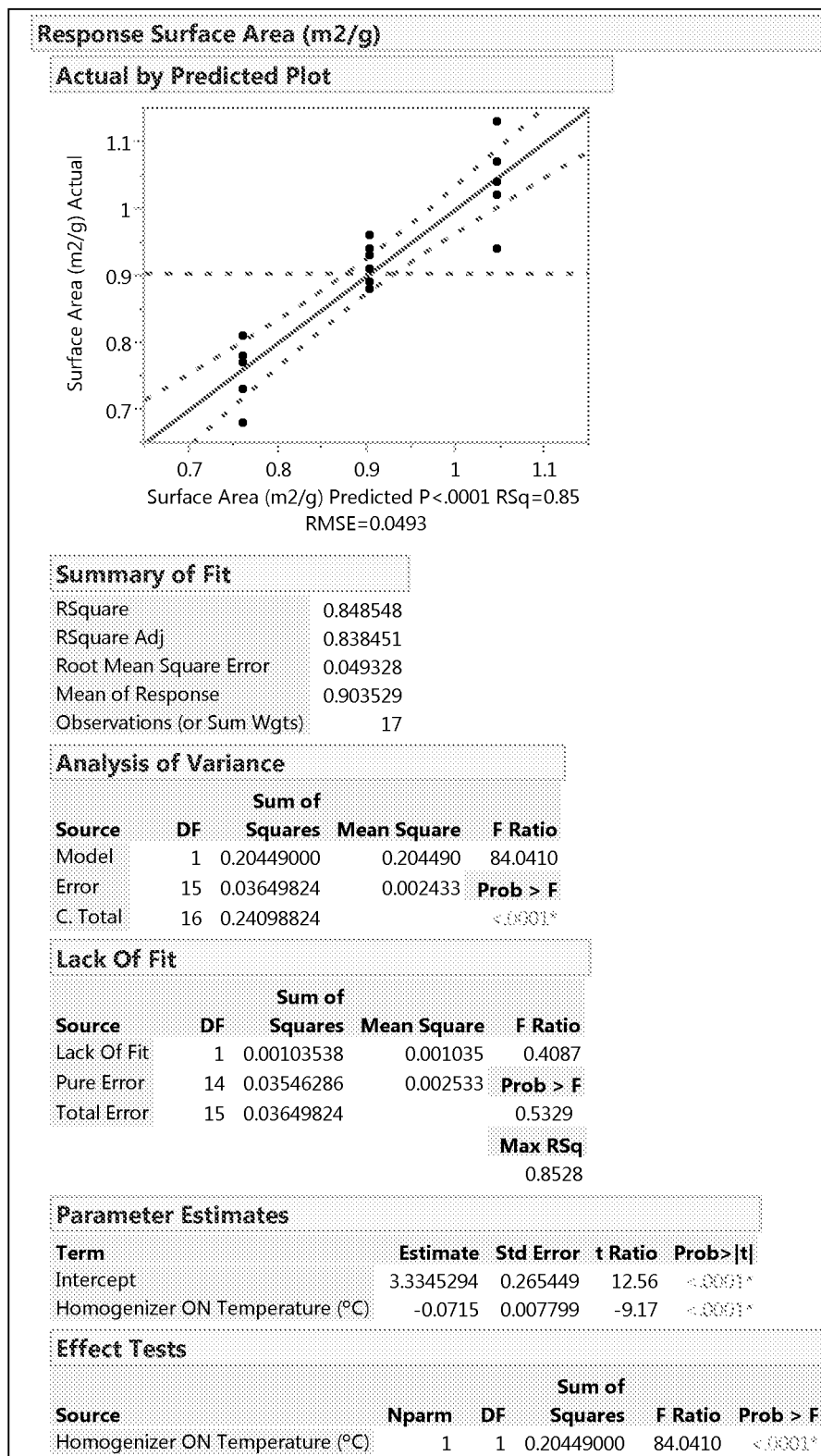
FIGS. 6, 7, 8, 9, and 10 show models built from the results of an augmented multi-factor DOE study used to evaluate the combinatory effect of homogenizer initiation temperature, homogenizer speed, and heat transfer temperature gradient on in-process crystal surface area, particle size, and exotherm onset temperature.
Figure 7:
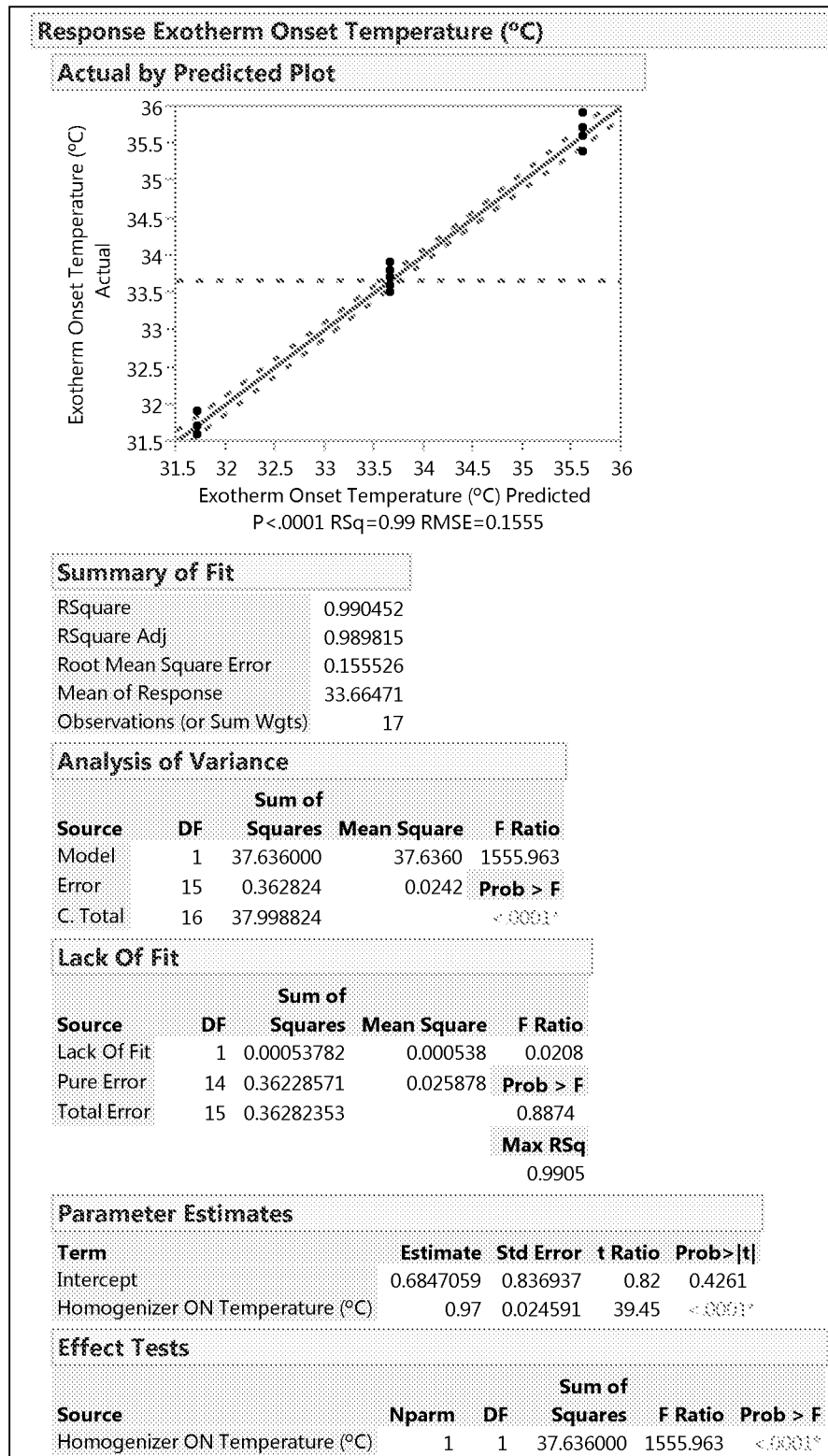
Figure 8:
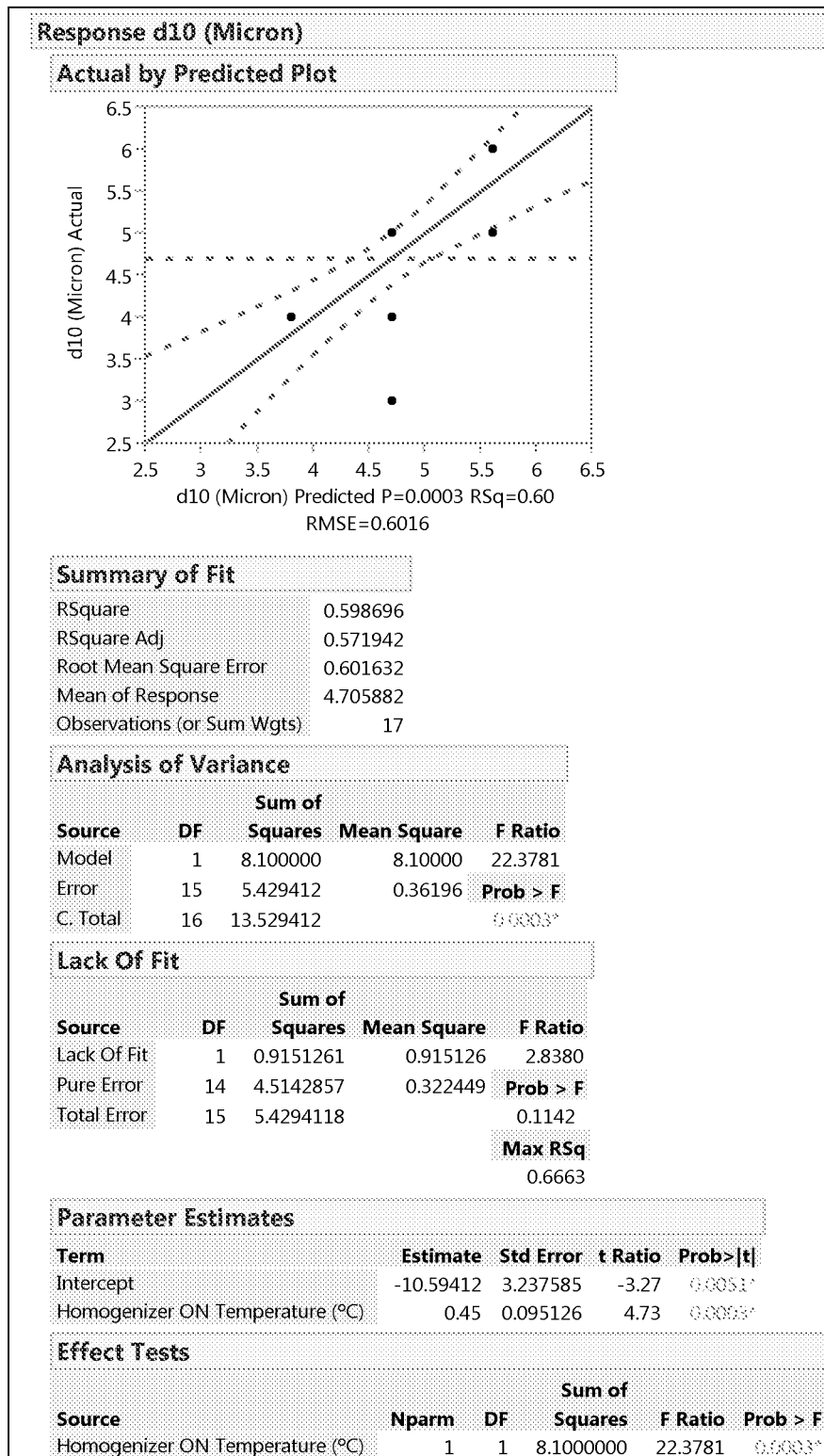
Figure 9:
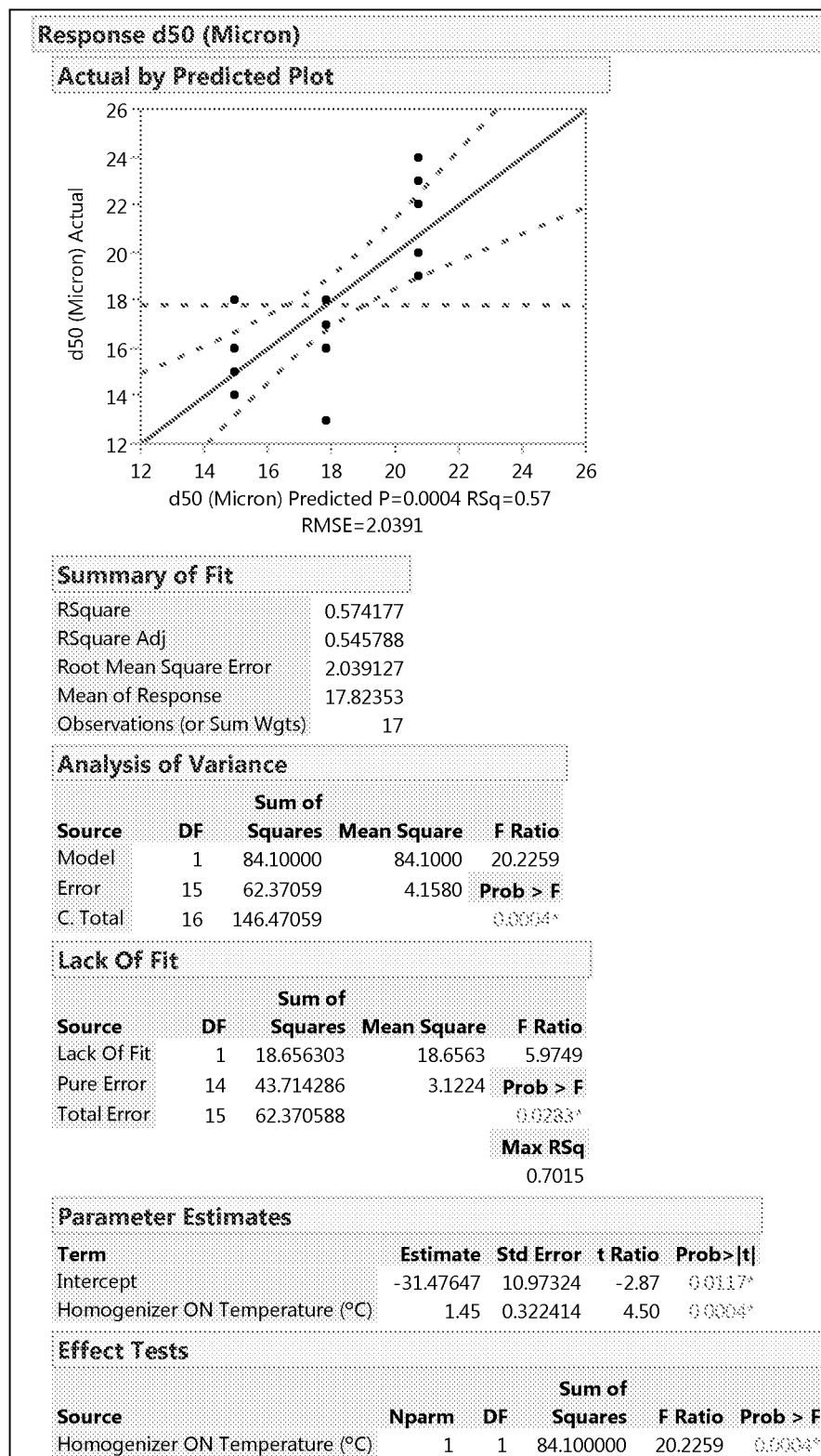
Figure 10:
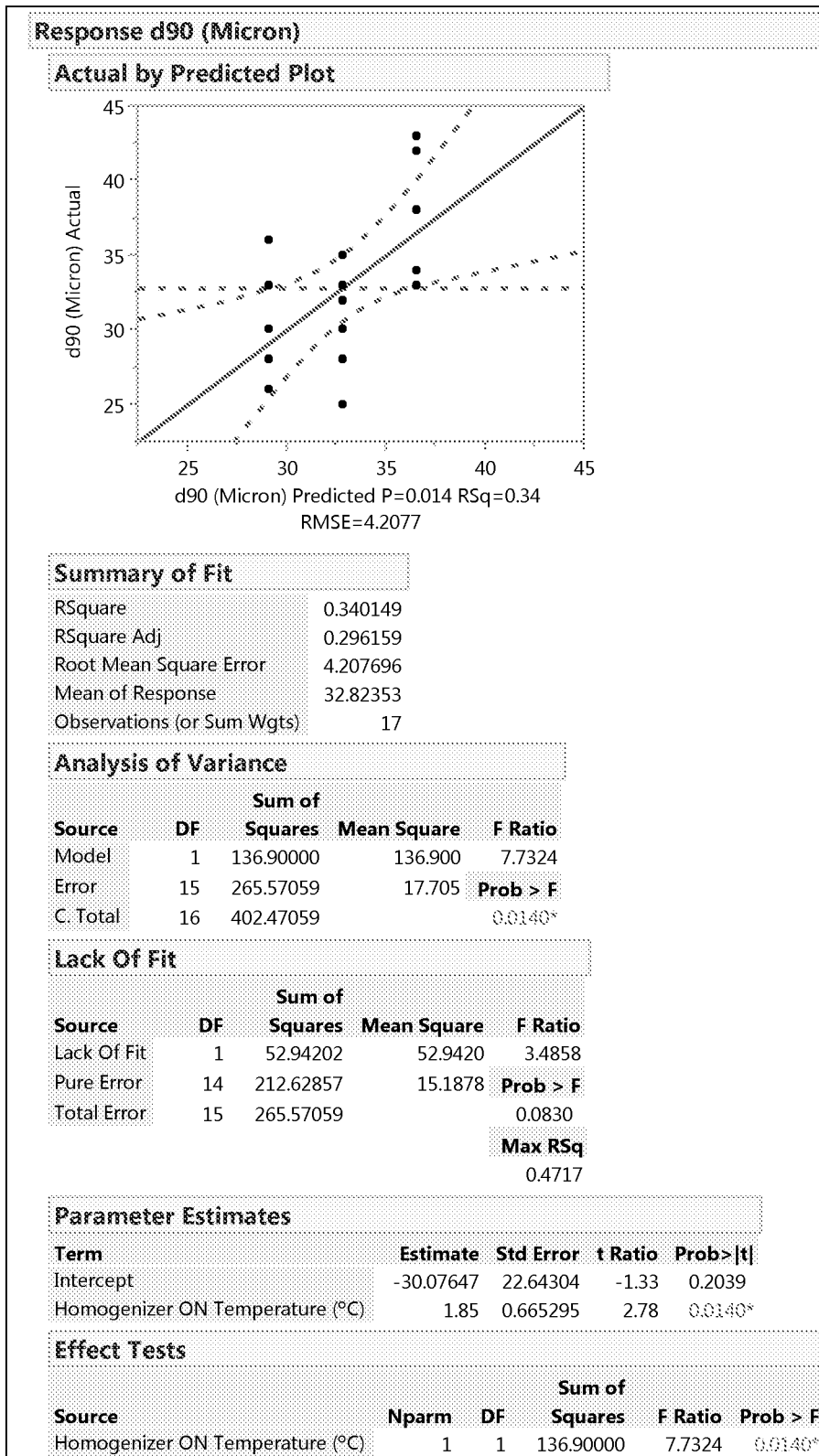

| FIG. | R² | ANOVA (p-value) | Lack of Fit |
|---|---|---|---|
| FIG. 6: Surface area Model (Multi-factor Augmented DOE) | 0.849 | <0.0001 | No |
| FIG. 7: Exotherm Onset Temperature Model (Multi-factor Augmented DOE) | 0.990 | <0.0001 | No |
| FIG. 8: Particle Size (Dv[10]) Model (Multi-factor Augmented DOE) | 0.599 | 0.0003 | No |
| FIG. 9: Particle Size (Dv[50]) Model (Multi-factor Augmented DOE) | 0.574 | 0.0004 | Yes |
| FIG. 10: Particle Size (Dv[90]) Model (Multi-factor Augmented DOE) | 0.340 | 0.0140 | No |

Characterization of the Process Operational zone (Multi-Factor DOE)

Figure 12:
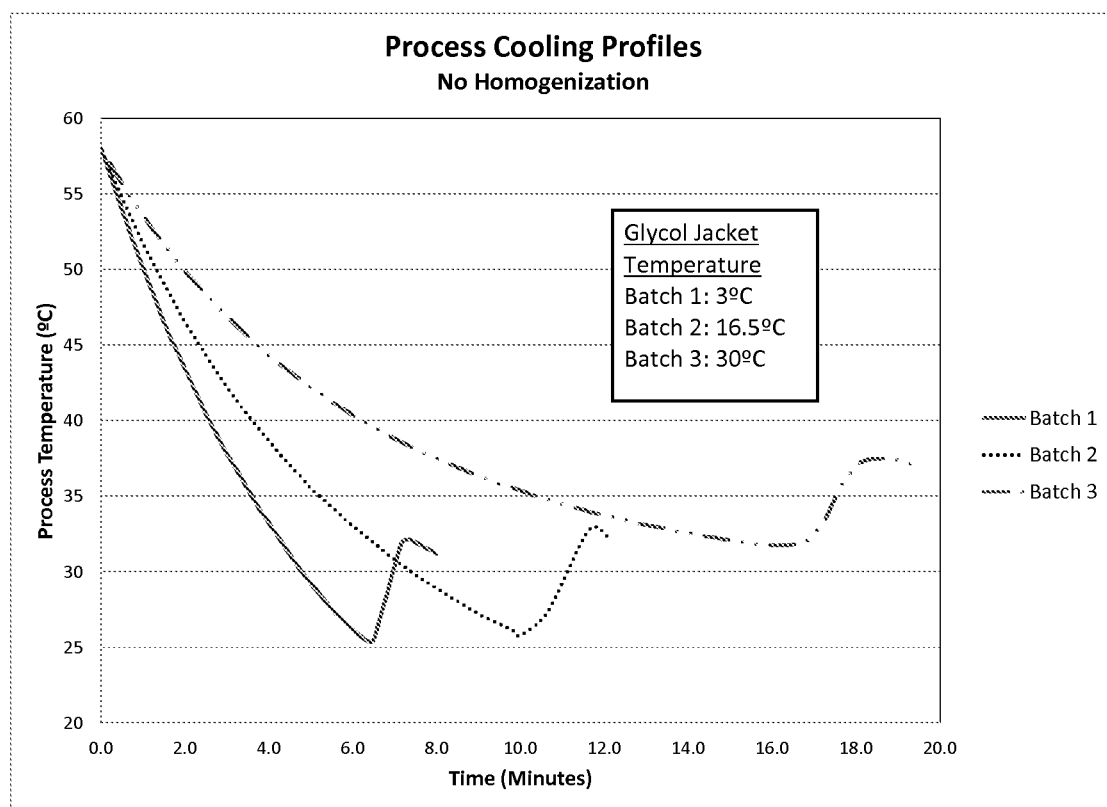
FIG. 12 shows several cooling profiles for runs from a multi-factor DOE (central composite design) study that used no homogenization.

The objective of this study was to characterize the impact of solution cooling rate (as a function of jacket glycol temperature), homogenization speed, and crystallization then continued to cool with homogenization until it crystallized. FIG. 12 shows several cooling profiles for runs that used no homogenization.

An exotherm onset temperature (Tmin) was recorded for each run and the cooling rate was calculated. The process cooling followed an exponential decay profile. Therefore, an Exponential Primary Cooling Parameter (i.e., cooling rate) was calculated by plotting the process temperature as a function of time using the following data transformation method:

$$y = m*x + b$$

Where:

$$y = -Ln\left[\frac{T - Ta}{To - Ta}\right]$$

$$x[ = ]Time(Min.)$$

$$T[ = ]Temperature(°C.)$$

$$To = 58° C.$$

$$Ta = 20° C.$$

Figure 13:
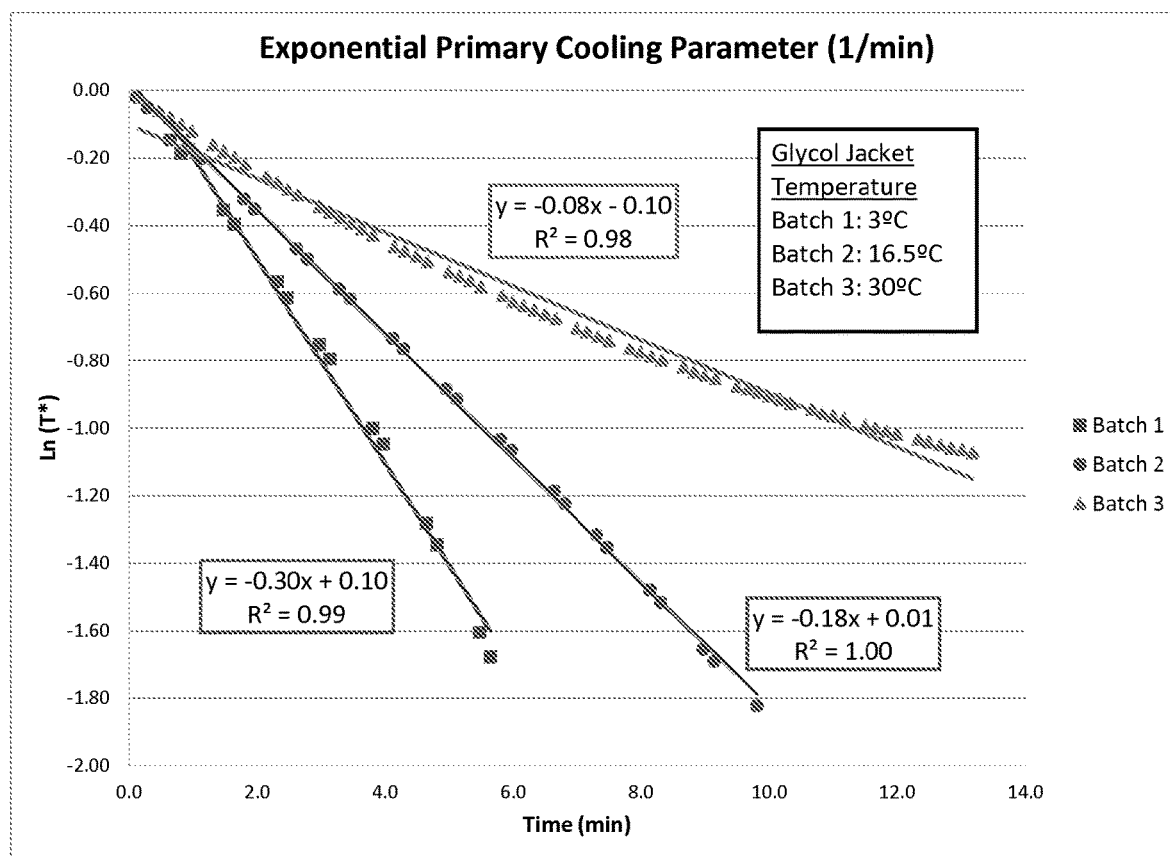
FIG. 13 shows plots of transformed temperature data for the cooling profiles from FIG. 12.

A linear-regression fit of the data resulted in slope-m (1/° C.) and intercept-b, where slope represents the Exponential Primary Cooling Parameter. FIG. 13 displays plots of the transformed temperature data for the corresponding cooling profiles from FIG. 12.

TABLE 6

Process Operational Zone Results

| Test ID | Homg. Setting (%) | Homg. ON Temp. (° C.) | Glycol Jacket Temp. (° C.) | Exponential Primary Cooling Parameter (1/min) | Exotherm Onset Temp. (° C.) | Induction Time (min) |
|---|---|---|---|---|---|---|
| F1 | 0 | N/A | 3 | 0.30 | 25.4 | 6.2 |
| F2 | 0 | N/A | 16.5 | 0.18 | 25.7 | 9.8 |
| F3 | 0 | N/A | 30 | 0.08 | 32.7 | 15.6 |
| F4 | 37.5 | 53.6 | 3 | 0.26 | 33.2 | 3.6 |
| F5 | 37.5 | 53.6 | 16.5 | 0.18 | 34.9 | 5.4 |
| F6 | 37.5 | 53.6 | 16.5 | 0.18 | 35.2 | 4.7 |
| F7 | 37.5 | 53.6 | 30 | 0.10 | 37.4 | 7.4 |
| F8 | 75 | 53.6 | 3 | 0.25 | 32.6 | 4.1 |
| F9 | 75 | 53.6 | 16.5 | 0.17 | 34.7 | 5.3 |
| F10 | 75 | 53.6 | 30 | 0.09 | 37.4 | 8.3 |

Figure 14:
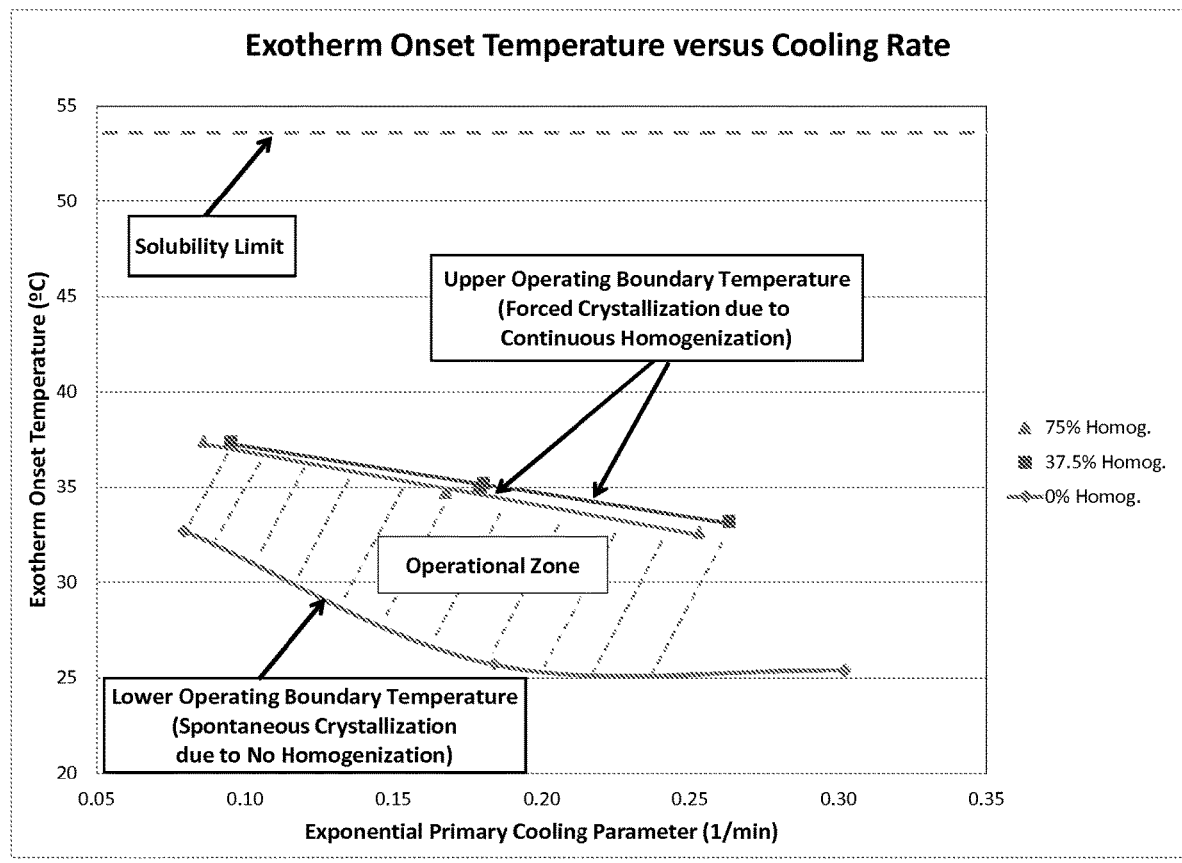
FIG. 14 shows a plot of exotherm onset temperature (Tmin) versus the calculated Exponential Primary Cooling Parameter (i.e., cooling rate).

FIG. 14 shows a plot of exotherm onset temperature (Tmin) versus the calculated Exponential Primary Cooling Parameter (i.e., cooling rate). The following terms describe key features of the plot:

Solubility Limit: The temperature at which the process solution becomes saturated. Below this temperature, the solution is supersaturated. The supersaturated solution is kinetically persistent since it is changing relatively slowly but has not yet reached thermodynamic equilibrium, which results in crystallization.

Lower Operating Boundary: The lowest process temperature the system can achieve at a specified cooling rate prior to spontaneous crystallization (i.e., crystallization in the absence of homogenization).

Upper Operating Boundary: The highest process temperature the system can achieve at a specified cooling rate prior to forced crystallization (i.e., crystallization that occurs in the presence of homogenization). In this case, homogenization was initiated immediately after the solution cooled to the solubility limit (53.6° C.), thereby imparting the maximum homogenization time within the meta-stable zone.

Operational Zone: The temperature range available to the system for a specified cooling rate where crystallization of the supersaturated solution can be induced through homogenization at a target temperature. The operational zone provided guidance for selection of optimum target cooling rate and exotherm onset temperature (Tmin) combinations, which resulted in robust processing to target surface areas.

Additional Synthesis Examples

200 Gram Scale

Aripiprazole lauroxil was recrystallized using the following procedure. 246.4 g of isopropyl acetate was heated in a 1 liter Erlenmeyer flask to 70-75° C. 383.0 g of heptane was heated in a 1 liter Erlenmeyer flask to 45-50° C. The hot isopropyl acetate was added to a 2 liter Erlenmeyer flask containing 200 g of aripiprazole lauroxil. The mixture was heated with swirling until all the white solids dissolved and a clear solution was obtained at 65-70° C. Hot heptane was added to the clear solution in three portions with gentle heating and swirling to avoid crash-out.

The flask containing the clear solution was placed in a 12 inch sieve pan or equivalent. A homogenizer probe was placed into the solution and turned on to #3 (13.5 1/min set on the machine). Ice was added up to the capacity of the pan. The homogenizer was stopped once the solution crystallized. The flask was kept in ice until the temperature was 15-20° C. The flask was removed from the ice bath.

A filtration set-up was assembled using a 2 liter filtering flask, Buchner funnel with a rubber connector, and filter paper. The filter paper was wetted with heptane (~5 ml). The recrystallized white solid was filtered and washed with heptane (~60 ml).

The filtered material was spread into a dish. The material was dried inside a vacuum oven at room temperature for 18-24 hrs with a nitrogen purge. The dried material was transferred into a 250 μm sieve. 5 PTFE sieve rings were added to the sieve, a cover with o-ring was placed on the sieve, and sieving took place using an Analysette 3 PRO at an amplitude set point of 2.7.

Figure 15:
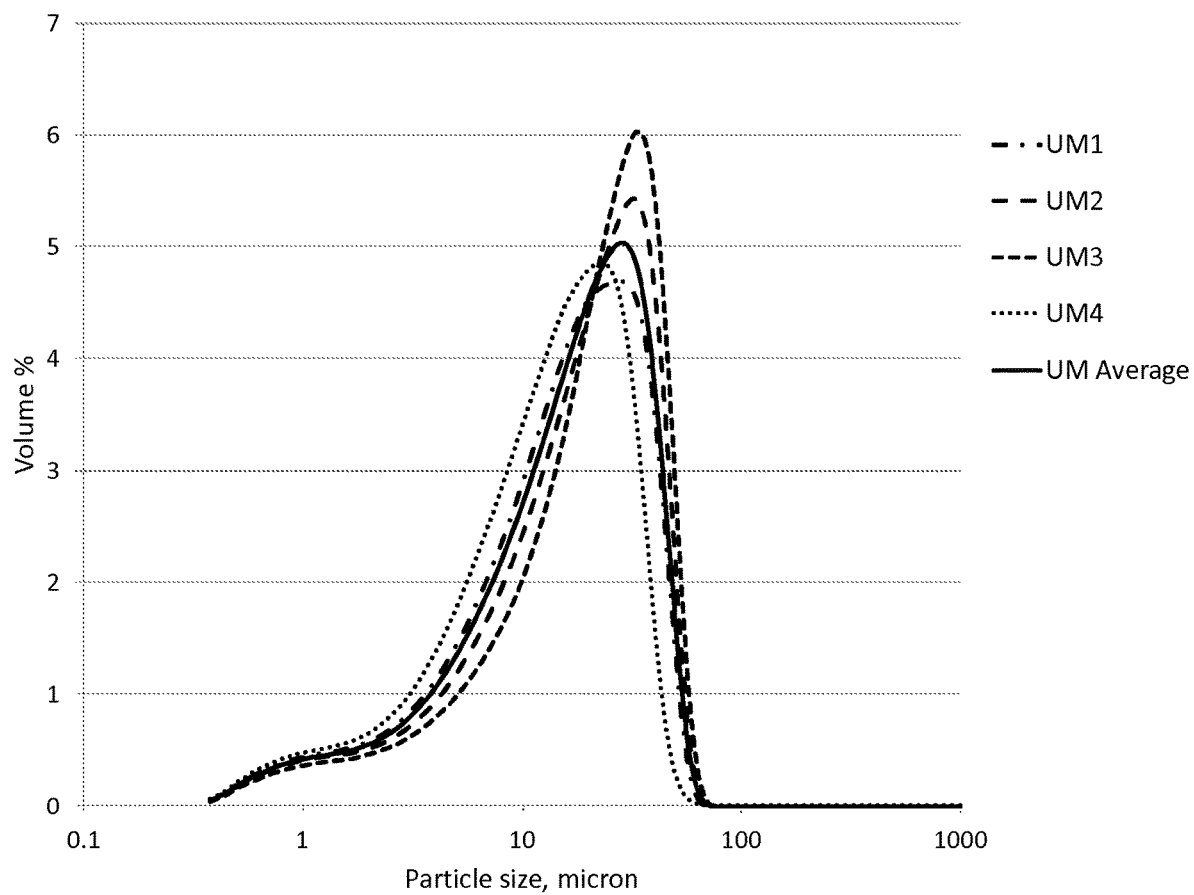
FIG. 15 shows particle size distributions for several batches of recrystallized aripiprazole lauroxil made according to a 200 gram process.

Four batches were made following this procedure and combined together to prepare a suspension of aripiprazole lauroxil. Table 7 lists the particle size distribution summary statistics for each batch as well as the combined (weight averaged) final batch. FIG. 15 shows the particle size distributions for each batch as well as the combined (weight averaged) final batch.

TABLE 7

Particle size distribution summary statistics (post dry and sieving)

| Batch | Dv[10], μm | Dv[50], μm | Dv[90], μm | % Total |
|---|---|---|---|---|
| UM1 | 3 | 17 | 39 | 23.5 |
| UM2 | 4 | 20 | 42 | 22.4 |
| UM3 | 4 | 23 | 45 | 22.1 |
| UM4 | 3 | 14 | 33 | 32.0 |
| UM Average | 3 | 18 | 39 | 100 |

Modified 200 Gram Scale

Using a graduated cylinder, 280 ml of isopropyl acetate were measured and transferred to a 2 liter Erlenmeyer flask. Using a graduated cylinder, 560 ml of n-heptane were measured and mixed with the measured isopropyl acetate. 200 g of aripiprazole lauroxil were weighed into a 2 liter Erlenmeyer flask. The solvent mixture was heated to 70° C. and then added to the aripiprazole lauroxil containing flask. The slurry was heated back to 65° C. to obtain a clear solution.

The solution was then poured into a 1 liter jacketed glass vessel with a first recirculator recirculating water and an overhead high shear mixing probe. The probe was turned on immediately on setting #3 (13.5 1/min set on the machine). As soon as the internal temperature reached 2° C. above the target arrest temperature, the recirculating water was switched to a second recirculator in order to arrest the cooling. As soon as the temperature started to rise the time was noted and the recirculating water was switched back to the first recirculator. The probe was then stopped 90 seconds after the start of the temperature rise, after which it was replaced with an overhead mixer. The slurry was left to cool down to 18° C.

When the slurry reached 18° C. the slurry was filtered using a Buchner funnel with Whatman filter paper 4. The solids were then washed with approximately 100 ml of n-heptane. The solids were spread into a crystallization dish and left to dry in a vacuum oven at room temperature, house vacuum, and a nitrogen purge for approximately 18 hours.

TABLE 8

Differences between 200 g scale and modified 200 g scale processes

| | 200 gram scale | Modified 200 gram process |
|---|---|---|
| Drug dissolution | Aripiprazole lauroxil is dissolved in 70-75° C. isopropyl acetate and then 45-50° C. heptane is added. | Aripiprazole lauroxil is dissolved in a 65° C. isopropyl acetate/heptane mixture. |
| Crystallization vessel | 2 liter Erlenmeyer flask in an ice bath. | 1 liter jacketed glass vessel with two recirculating jacket fluid temperatures. |
| Mixing Crystallization | Manual swirling and homogenizer. Homogenizer is switched on and solution is cooled with ice bath until it reaches 15-20° C. Homogenizer is switched off once the solution crystallizes, | Overhead mixer and homogenizer. Homogenizer is switched on and solution cooled with recirculator 1. As soon as the internal temperature reached 2° C. above the target arrest temperature, the recirculating water is switched to recirculator 2 in order to arrest the cooling. As soon as the temperature started to rise the time the recirculating water is switched back to recirculator 1 until the slurry reaches 15-20° C. Homogenizer is switched off 90 s after the start of the temperature rise, after which it is replaced with an overhead mixer. |

Figure 16:
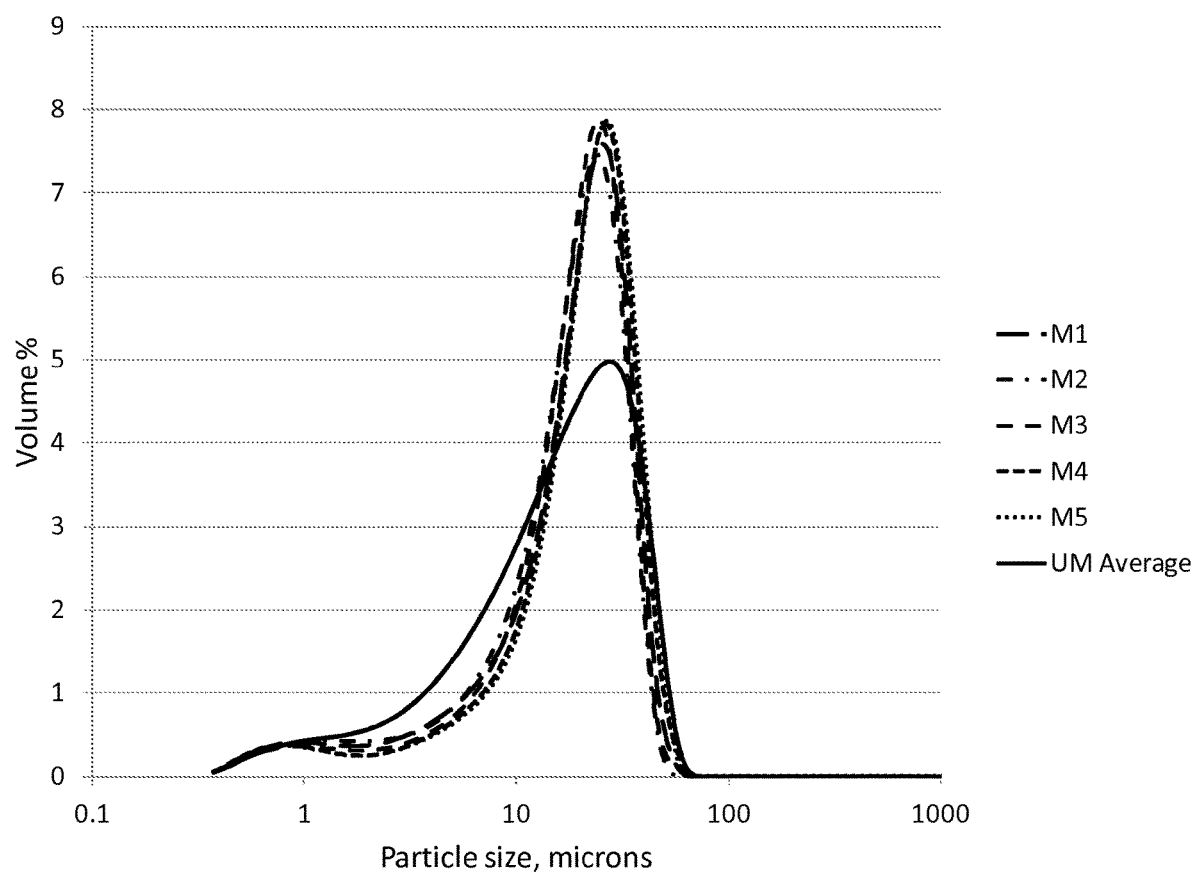
FIG. 16 shows particle size distributions for several batches of recrystallized aripiprazole lauroxil made according to a modified 200 gram process.

The modified 200 gram process was used successfully in four aripiprazole lauroxil recrystallization batch campaigns (each consisting of five recrystallization batches). A particle size distribution similar to that from the (unmodified) 200 gram process was reproducibly obtained as seen in FIG. 16. Summary statistics are listed in Table 9. A comparison between the particle size distribution statistics of recrystallized aripiprazole lauroxil from the modified process versus that from the unmodified process revealed a tighter spread in Dv[10], Dv[50], and Dv[90], clearly showing an improvement in process robustness and reproducibility.

TABLE 9

Particle size distribution summary statistics of four batch campaigns

| Batch | Dv[10], µm | Dv[50], µm | Dv[90], µm |
|---|---|---|---|
| M1 | 5 | 21 | 36 |
| M2 | 4 | 20 | 34 |
| M3 | 6 | 21 | 35 |
| M4 | 6 | 23 | 39 |
| M5 | 6 | 23 | 39 |
| 2A | 6 | 21 | 36 |
| 2B | 6 | 23 | 39 |
| 2C | 7 | 26 | 42 |
| 2D | 7 | 23 | 38 |
| 2E | 5 | 21 | 36 |
| 3A | 7 | 24 | 40 |
| 3B | 6 | 23 | 39 |
| 3C | 6 | 22 | 38 |
| 3D | 6 | 23 | 39 |
| 3E | 6 | 23 | 41 |
| 4A | 6 | 22 | 37 |
| 4B | 6 | 24 | 39 |
| 4C | 4 | 20 | 34 |
| 4D | 4 | 21 | 37 |
| 4E | 4 | 22 | 37 |
| Range | 4-7 | 20-26 | 34-42 |
| Mean | 6 | 22 | 38 |
| Rel. SD | 17% | 7% | 6% |

1.75 kg Scale

Aripiprazole lauroxil was recrystallized using the following procedure. 2156.0 g of isopropyl acetate was added to a recrystallization vessel containing 1750.0 g of aripiprazole lauroxil. The mixture was heated under agitation to 55-65° C. When the drug was visibly dissolved in solution, 3351.0 g of heptane heated to 55-65° C. was added to the recrystallization vessel. The resulting mixture was heated to 60-65° C., at which point cold glycol was introduced into the jacket of the recrystallization vessel in order to cool the mixture. When the temperature of the mixture of isopropyl acetate, heptane, and aripiprazole lauroxil reached 34° C., homogenization was initialized. The temperature was continuously monitored for the onset of the exotherm (start of precipitation or crystallization) and the exotherm maximum. When the mixture temperature reached the value Tmin after the exotherm (Tmin$_2$), homogenation was stopped. More cold glycol was introduced into the vessel jacket in order to cool the mixture to 18° C., at which point the mixture was held for 5 minutes.

Then, hot glycol was introduced into the vessel jacket to reheat the mixture toward 60-65° C., at which point cold glycol was again introduced into the jacket of the recrystallization vessel in order to cool the mixture. When the temperature of the mixture of isopropyl acetate, heptane, and aripiprazole lauroxil reached 34° C., homogenization was initialized. The temperature was continuously monitored for the onset of the exotherm and the exotherm maximum. When the mixture temperature reached the value Tmin after the exotherm (Tmin$_2$), homogenation was stopped. More cold glycol was introduced into the vessel jacket in order to cool the mixture to 18° C. The recrystallized aripiprazole lauroxil was filtered under vacuum in a dead end filter dryer and rinsed with 2187.0 g of heptanes at ambient temperature. The solids were dried under vacuum (80 torr) for 40 hours in the same vessel and collected.

4 kg Scale

Aripiprazole lauroxil was recrystallized using the following procedure. 4940.0 g of isopropyl acetate was added to a recrystallization vessel containing 4000.0 g of aripiprazole lauroxil and mixture under agitation. When the drug was visibly dissolved in solution (≥55° C.), 7670.0 g of heptane heated to 55-65° C. was added to the recrystallization vessel. The resulting mixture was heated to ≥60° C. and then held for 5 minutes. Cold glycol (28° C.) was then introduced into the jacket of the recrystallization vessel in order to cool the mixture, and when the temperature of the mixture of isopropyl acetate, heptane, and aripiprazole lauroxil reached 33.8° C., homogenization was initialized. The temperature was continuously monitored for the onset of the exotherm (start of precipitation or crystallization) and the exotherm maximum. (If Tmin was less than 33° C., then another cycle of recrystallization was performed.) When the mixture temperature reached the value Tmin after the exotherm (Tmin$_2$), the homogenation was stopped. More cold glycol was introduced into the vessel jacket in order to cool the mixture to 18° C.

Then, hot glycol was introduced into the vessel jacket to reheat the mixture toward 60-65° C., at which point cold glycol was again introduced into the jacket of the recrystallization vessel in order to cool the mixture. When the temperature of the mixture of isopropyl acetate, heptane, and aripiprazole lauroxil reached 33.8° C., homogenization was initialized. The temperature was continuously monitored for the onset of the exotherm and the exotherm maximum. When the mixture temperature reached the value Tmin after the exotherm (Tmin$_2$), homogenization was stopped. More cold glycol was introduced into the vessel jacket in order to cool the mixture to 18° C. The recrystallized aripiprazole lauroxil was filtered under vacuum in a dead end filter dryer and rinsed with 9 kg of heptanes at ambient temperature. The solids were dried under vacuum (20 torr) for 20 hours in the same vessel and collected.

Example Using Sonication Instead of Homogenization

Aripiprazole lauroxil (10 g) was dissolved in hot isobutyl acetate (14 mL). N-heptane (28 mL) was added to the hot solution and the mixture was heated further to dissolve all solids. The hot solution was placed in a sonication bath and sonicated for 2 minutes. Ice was added to the sonication bath to cool down the mixture. White crystals were formed. The crystals were filtered using a Buchner funnel and washed with cold n-heptane (10 mL). The white solid was then dried under vacuum at room temperature overnight and resulted in 9.6 g of recrystallized aripiprazole lauroxil (96% yield).

Impact of Aripiprazole Lauroxil Particle Size Distribution (PSD), Surface Area, and Vehicle on In Vivo Release Profiles In order to explore the effect of injection vehicle on aripiprazole plasma exposure, a single-dose IM (intramuscular) rat dosing study was conducted. The dosing amount in the study was 29 mg of recrystallized aripiprazole lauroxil prodrug, which is equivalent to 20 mg aripiprazole base. The following two formulations were prepared and dosed intramuscularly to male rats:

(1) aripiprazole lauroxil bulk recrystallized drug substance suspended in a phosphate-buffered saline injection vehicle with sodium carboxymethylcellulose (NaCMC) (2 wt %) and polysorbate 20 (0.2 wt %); and
(2) aripiprazole lauroxil recrystallized drug substance suspended in a phosphate-buffered saline injection vehicle using sorbitan monolaurate (SML) (0.5 wt %) and polysorbate 20 (0.2 wt %).

Figure 17:
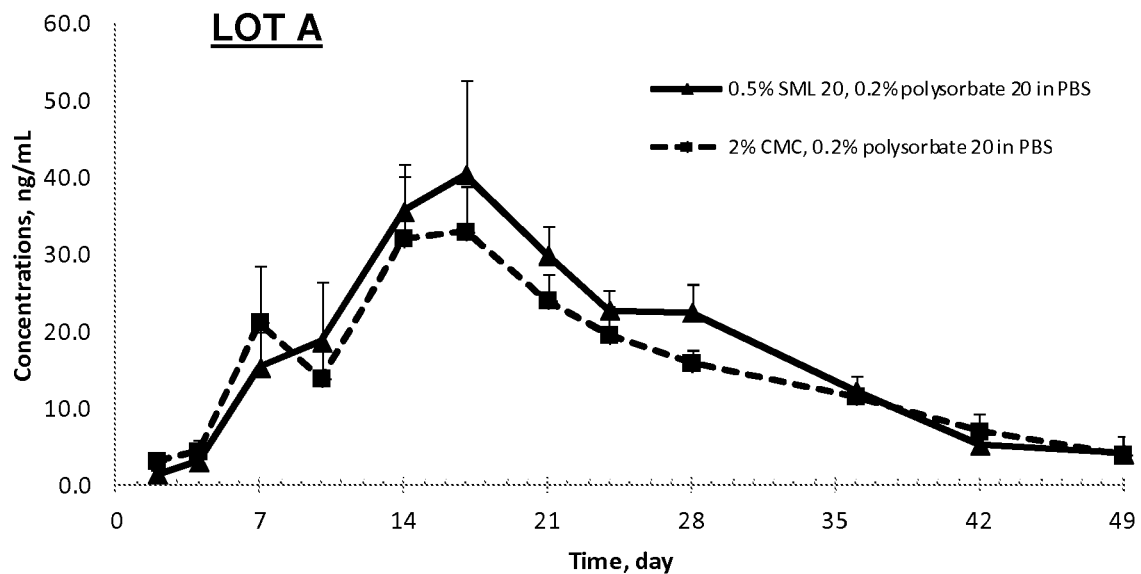
FIG. 17 shows aripiprazole pK profiles resulting from intramuscular administration of a single dose of recrystallized aripiprazole lauroxil (20 mg aripiprazole equivalents) suspended in either NaCMC or SML vehicle, to male rats to assess the effect of injection vehicle on the in vivo profile.
Figure 17:
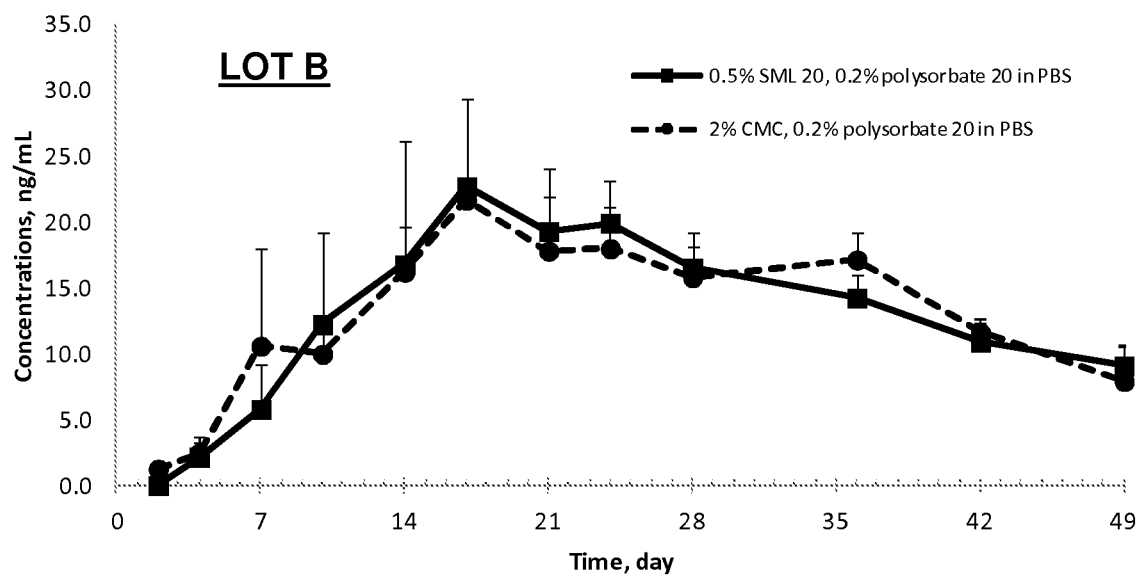

FIG. 17 shows pharmacokinetic profiles of aripiprazole resulting from intramuscular administration of a single dose of recrystallized aripiprazole lauroxil (20 mg aripiprazole equivalents) suspended in either the NaCMC or SML vehicle, to male rats to assess the effect of injection vehicle on the in vivo profile. Two lots of recrystallized aripiprazole lauroxil drug substance were tested. Pharmacokinetic analysis showed that suspensions prepared from the same drug substance lot resulted in essentially overlapping in vivo pK profiles of aripiprazole, independent of injection vehicle.

The pK parameters, summarized in Table 10, indicated that the injection vehicle did not significantly impact $C_{max}$, $T_{max}$, or $AUC_{0-Tlast}$.

TABLE 10 pK parameters from a single IM administration of recrystallized aripiprazole lauroxil in male rats

| drug substance lot, vehicle | $C_{max}$ (ng/mL)[a] | $T_{max}$ (day)[b] | $AUC_{0-Tlast}$[c] (day * ng/mL) |
|---|---|---|---|
| Lot A, suspended in NaCMC vehicle | 34.2 ± 6.21 | 13.8 ± 3.66 | 735 ± 82.7 |
| Lot A, suspended in SML vehicle | 43.1 ± 8.60 | 16.0 ± 1.55 | 836 ± 73.0 |
| Lot B, suspended in NaCMC vehicle | 22.7 ± 1.17 | 17.2 ± 5.74 | 638 ± 53.7 |
| Lot B, suspended in SML vehicle | 23.4 ± 6.47 | 17.2 ± 3.66 | 643 ± 146 |

[a]$C_{max}$: The maximum precipitated plasma concentration observed.
[b]$T_{max}$: Time at which $C_{max}$ occurred.
[c]$AUC_{0-tlast}$: Area under the precipitated plasma concentration-time curve from Time 0 to the last measured precipitated plasma concentration.

Figure 18:
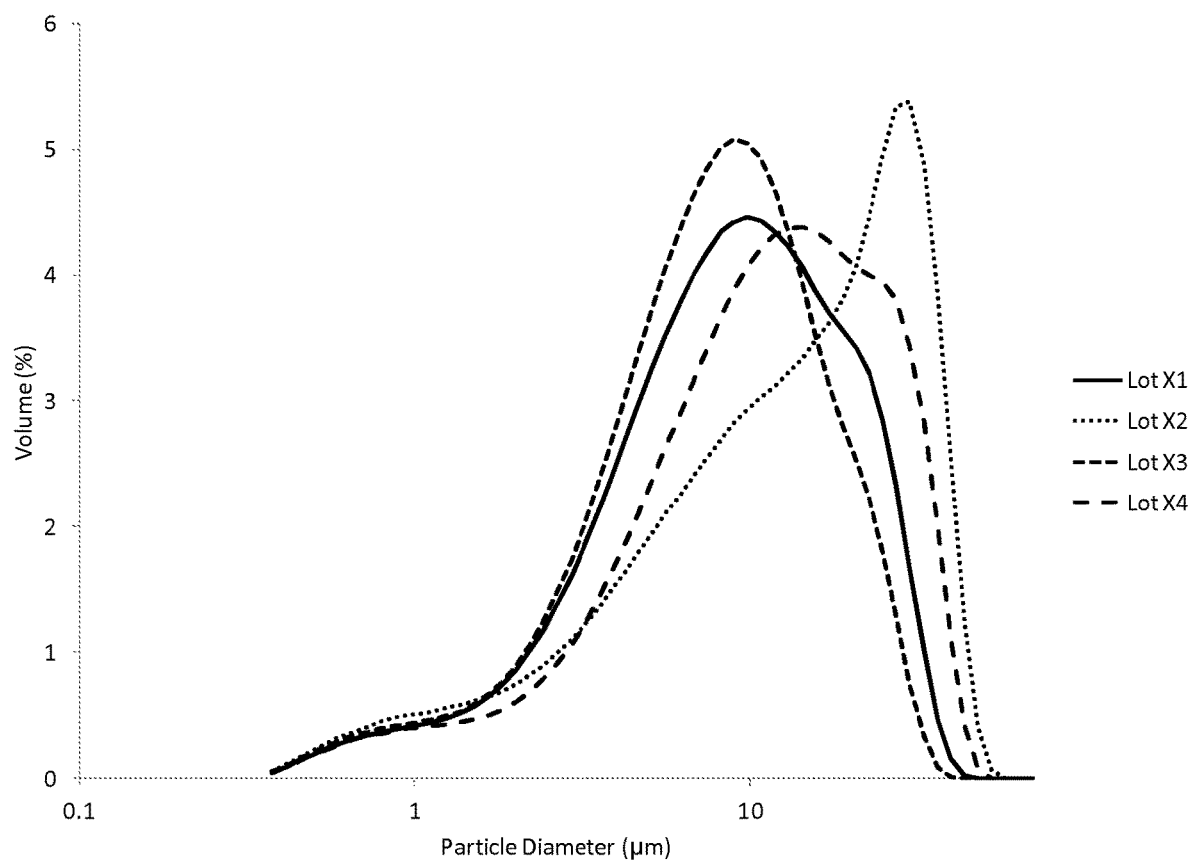
FIG. 18 shows particle size distribution (PSD) profiles for four lots of aripiprazole lauroxil recrystallized drug substance.

The impact of the particle size distribution (PSD) and surface area on aripiprazole pK was further investigated using four lots of recrystallized aripiprazole lauroxil in the rat IM pK model at the same dose of 29 mg aripiprazole lauroxil equivalent to 20 mg of aripiprazole. PSD and surface area measurements for the four lots are presented in Table 11, and the PSD profiles are illustrated in FIG. 18.

TABLE 11

PSD and surface area measurements for aripiprazole lauroxil bulk recrystallized drug substance lots

| Lot # | Dv[10] μm[a] | Dv[50] μm[a] | Dv[90] μm[a] | Surface area (m²/g) |
|---|---|---|---|---|
| X2 | 3 | 15 | 35 | 0.73 |
| X1 | 3 | 9 | 24 | 1.10 |
| X3 | 3 | 8 | 20 | 1.32 |
| X4 | 3 | 12 | 30 | Not measured |

[a]For a single preparation and measurement, PSD method error for the volume metrics are: Dv[10] = ±0.9 μm, Dv[50] = ±3.5 μm, and Dv[90] = ±5.7 μm. For an average of three preparations and measurements, PSD method error would be Dv[10] = ±0.5 μm, Dv[50] = ±2.0 μm, and Dv[90] = ±3.3 μm.

Figure 19:
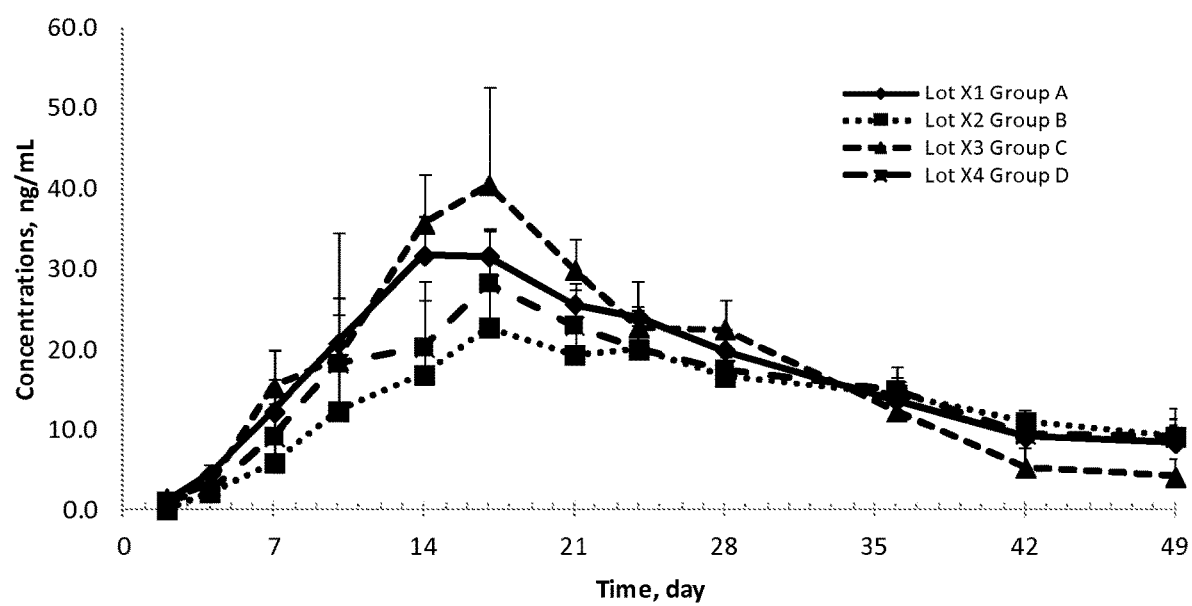
FIG. 19 shows aripiprazole pK profiles resulting from IM administration to male rats of recrystallized aripiprazole lauroxil from the same lots as in FIG. 18 suspended in SML vehicle.

To examine the influences of the PSD and surface area on aripiprazole pK, the characterized lots of recrystallized aripiprazole lauroxil listed in Table 11 were suspended in SML vehicle and administered by IM administration to male rats. The aripiprazole pK profiles are plotted in FIG. 19, and the pK parameters are presented in Table 12. These data show that material with a smaller PSD and increased surface area (i.e., lot X3) will result in faster release rates (FIG. 19, top-most curve). (Release rate is expressed as aripiprazole plasma exposure (dependent on both the rate of dissolution of recrystallized aripiprazole lauroxil and the rate of esterase mediated conversion of aripiprazole lauroxil to aripiprazole). Material with larger PSD and decreased surface area (i.e., lot X2) will result in slower release rates (FIG. 19, bottom-most curve). Importantly, examination of the calculated $AUC_{inf}$ indicates that systemic exposure was similar for all groups in this experiment.

TABLE 12

Aripiprazole pK parameters following a single IM administration of recrystallized aripiprazole lauroxil suspended in SML injection vehicle in male rats

| Drug Lot | Group | Surface area (m²/g) | | $C_{max}$[a] (ng/mL) | $T_{max}$[b] (day) | $AUC_{0-tlast}$[c] (day*ng/mL) | $AUC_{inf}$[d] (day*ng/mL) |
|---|---|---|---|---|---|---|---|
| Lot X3 | C | 1.32 | Mean | 43.1 | 16.0 | 836 | 894 |
|  |  |  | SD | 8.60 | 1.55 | 73.0 | 91 |
| Lot X1 | A | 1.10 | Mean | 35.0 | 15.5 | 817 | 1050 |
|  |  |  | SD | 6.76 | 3.73 | 66.7 | 157 |
| Lot X4 | D | Not measured | Mean | 28.9 | 16.0 | 713 | 952 |
|  |  |  | SD | 6.23 | 1.55 | 153.0 | 282 |
| Lot X2 | B | 0.73 | Mean | 23.4 | 17.2 | 643 | 918 |
|  |  |  | SD | 6.47 | 3.66 | 146.0 | 184 |

[a] $C_{max}$: The maximum precipitated plasma concentration observed.
[b] $T_{max}$: Time at which $C_{max}$ occurred.
[c] $AUC_{0-tlast}$: Area under the precipitated plasma concentration-time curve from Time 0 to the last measured precipitated plasma concentration.
[d] $AUC_{inf}$: Area under the precipitated plasma concentration-time curve from Time 0 to infinity.

The conclusions from these experiments are that both PSD and surface area measurements were important aspects of the physical property characterization of the aripiprazole lauroxil drug crystals. Consistent with a release mechanism that is dominated by crystal dissolution, the data obtained from these pK studies highlight the rank order with regard to surface areas and pK profiles. This ordering is consistent with the character of the insoluble prodrug crystals, namely, that the particle size distribution and surface area of aripiprazole lauroxil are the key attributes influencing in vivo performance.

In conclusion, as demonstrated in the pK studies described above, the performance of recrystallized aripiprazole lauroxil drug product was dominated by the physical properties of the product crystals. Dissolution of aripiprazole lauroxil following injection was limited by slow dissolution of the drug crystals, and was a function of the amount of exposed surface area of the aripiprazole lauroxil material. The particle size distribution and surface area of aripiprazole lauroxil were the key attributes influencing in vivo performance.

Two-Pass Recrystallization

A two-pass recrystallization process was developed to further improve reproducibility and particle size control.

As described earlier, crystallization of aripiprazole lauroxil occurs after cooling the mixture of the drug, the first solvent (such as isopropyl acetate), and the second solvent (such as n-heptane) to a supersaturated condition. Control of the solution temperature to target a specific onset temperature (exotherm "Tminimum" or "Tmin") for crystallization is important to control the final particle size distribution and surface area of the aripiprazole lauroxil crystals. Nucleation and crystallization can be induced by initiating high-shear mixing as the supersaturated mixture approaches a target temperature. The recrystallization process of the present invention reproducibly produces crystals of aripiprazole lauroxil with desirable particle size distribution and surface area parameters.

Subsequent to the studies described above involving one-pass recrystallization or a single pass of recrystallization, additional studies were performed in ultra-clean equipment.

In sterile pharmaceutical manufacturing, processing is conducted in ultra-clean equipment to ensure quality and reduce contamination. Equipment is cleaned and steam sterilized in place before use. Surface finish is controlled to be very smooth to aid in cleaning. After cleaning and during use, equipment must be kept totally closed to the environment to prevent contamination. A first pass of recrystallization may not always behave as predictably as desired. For instance, variation in crystallization onset time or crystallization temperature may be unacceptably large, resulting in recrystallized particles that have sub-optimal particle size distribution and surface area parameters. Moreover, since the process is conducted in totally closed equipment, conventional means of adding solid crystals to facilitate crystallization can be highly impractical.

Accordingly, a process to further facilitate reproducible recrystallization of aripiprazole lauroxil was developed. Crystals of aripiprazole lauroxil were first formed by cooling and precipitating at supersaturated conditions with or without homogenization. The solution was then re-warmed and the crystals were re-dissolved. When the solution was re-cooled, crystals were precipitated in a reliable manner, with the aid of high-shear mixing as the target temperature was approached, much as in the one-pass crystallization process described earlier.

In replicate experiments, the first pass recrystallization resulted in large variation in time from homogenizer onset to crystal formation. Time to crystallization ranged from about 1 minute to over 37 minutes. A larger variation in crystallization Tmin was noted. Results of first pass recrystallization are shown in Table 13.

TABLE 13

| Sample # | Crystallization pass | Homogenizer ON time | Crystallization onset (Tmin) time | Induction time (Crystallization onset time- homogenizer on time) | Homogenizer ON temperature, °C. | Tmin, °C. |
|---|---|---|---|---|---|---|
| Z1 | 1 | 17:46 | 34:00 | 16:14 | 35 | 31.3 |
| Z2 | 1 | 16:37 | 17:35 | 0:58 | 35 | 34.6 |
| Z3 | 1 | 17:06 | 54:59 | 37:53 | 35 | 29.5 |

After seeding, the subsequent second pass of recrystallization occurred quickly and reproducibly around 1 minute or less after homogenization onset. A much smaller variation in Tmin was achieved. Results of the second pass of recrystallization are shown in Table 14.

TABLE 14

| Sample # | Crystallization pass | Homogenizer ON time | Crystallization onset (Tmin) time | Induction time (Crystallization onset time- homogenizer on time) | Homogenizer ON temperature, °C. | Tmin, °C. |
|---|---|---|---|---|---|---|
| Z1 | 2 | 17:03 | 18:05 | 1:02 | 35 | 34.6 |
| Z2 | 2 | 17:03 | 17:50 | 0:47 | 35 | 34.6 |
| Z3 | 2 | 17:22 | 17:49 | 0:27 | 35 | 34.8 |

While this invention has been particularly shown and described with references to preferred embodiments thereof, it will be understood in light of the present disclosure by those skilled in the art that various changes in form and details may be made therein without departing from the scope of the invention encompassed by the appended claims.

What is claimed is:

1. A process for making a compound of Formula (A) in crystal form:

Formula (A)

wherein $R^a$ is $CH_2OC(O)R^1$ and wherein $R^1$ is a substituted or unsubstituted aliphatic moiety;
the process comprising the steps of:
(a) dissolving the compound of Formula (A) or a salt or solvate thereof in a first solvent to form a homogeneous drug solution;
(b) optionally combining the drug solution with a second solvent;
(c) cooling the solution; and
(d) further homogenizing the solution to induce formation of the compound of Formula (A) in crystal form.

2. The process of claim 1, further comprising the steps of:
(e) stopping the homogenization, and re-dissolving the compound of Formula (A) in crystal form by heating the solution;
(f) cooling the solution; and
(g) further homogenizing the solution to induce formation of the compound of Formula (A) in crystal form.

3. The process of claim 1, wherein the crystallized particles have a surface area of about 0.50 to about 3.3 m²/g.

4. The process of claim 1, wherein the crystallized particles have a surface area of about 0.80 to about 1.1 m²/g.

5. The process of claim 1, wherein the crystallized particles have a surface area of about 1.00 m²/g.

6. The process of claim 1, wherein the Dv[50] of the crystallized particles is about 10 to about 30 microns.

7. The process of claim 1, wherein the Dv[50] of the crystallized particles is about 10 to about 20 microns.

8. The process of claim 1, wherein in step (a), the first solvent is isopropyl acetate.

9. The process of claim 1, wherein in step (a), the first solvent is a mixture of isopropyl acetate and n-heptane.

10. The process of claim 1, wherein in step (b), the second solvent is n-heptane.

11. The process of claim 1, wherein in step (b), the temperature of the solution is in the range of about 55° C. to about 65° C.

12. The process of claim 1, wherein in step (d), the temperature of the solution is within the range of about 31-38° C.

13. The process of claim 1, wherein in step (d), the temperature of the solution is within the range of about 31-35° C.

14. The process of claim 1, wherein in step (d), the temperature of the solution is about 34° C.

15. The process of claim 1, wherein one or more of steps (a) through (c) is performed under agitation.

16. The process of claim 2, wherein one or more of steps (a), (b), (c), (d), (e), (f), and (g) is performed under agitation.

17. The process of claim 1, wherein the process further comprises the step of filtering the crystallized particles.

18. The process of claim 17, wherein the process further comprises the step of rinsing the crystallized particles.

19. The process of claim 18, wherein the process further comprises the step of drying the crystallized particles.

20. The process of claim 1, wherein the compound of Formula (A) is selected from the group consisting of:

21. The process of claim 2, wherein the compound of Formula (A) is selected from the group consisting of:

Formula (I)

Formula (II)

and

Formula (I)

Formula (II)

22. The process of claim 1, wherein the solution of step (d) is further homogenized by a homogenizer.

23. The process of claim 20, wherein the compound of Formula (A) is a compound of Formula (I):

Formula (I)

24. The process of claim 21, wherein the compound of Formula (A) is a compound of Formula (I):

Formula (I)

* * * * *